(12) United States Patent
Bourne et al.

(10) Patent No.: US 7,611,542 B2
(45) Date of Patent: Nov. 3, 2009

(54) TISSUE TREATMENT

(75) Inventors: George Bourne, Southboro, MA (US);
Marcia S. Buiser, Watertown, MA (US);
Thomas V. Casey, II, Grafton, MA (US); Steve Keenan, Framingham, MA (US); Janel L. Lanphere, Pawtucket, RI (US); Jianmin Li, Lexington, MA (US);
Erin P. McKenna, Boston, MA (US);
Zarouhi Minasian, Bedford, MA (US);
Doreen Rao, Sudbury, MA (US)

(73) Assignee: Boston Scientific SciMed, Inc., Maple Grove, MN (US)

(*) Notice: Subject to any disclaimer, the term of this patent is extended or adjusted under 35 U.S.C. 154(b) by 423 days.

(21) Appl. No.: 11/555,413

(22) Filed: Nov. 1, 2006

(65) Prior Publication Data

US 2007/0059375 A1     Mar. 15, 2007

Related U.S. Application Data

(63) Continuation of application No. 10/231,664, filed on Aug. 30, 2002, now Pat. No. 7,131,997, which is a continuation-in-part of application No. 10/215,594, filed on Aug. 9, 2002, which is a continuation-in-part of application No. 10/109,966, filed on Mar. 29, 2002, now Pat. No. 7,094,369.

(60) Provisional application No. 60/388,446, filed on Jun. 12, 2002.

(51) Int. Cl.
*A61F 2/36* (2006.01)

(52) U.S. Cl. .................. 623/23.72; 623/23.76; 424/501
(58) Field of Classification Search .............. 623/23.72, 623/23.73, 23.74, 23.76; 424/501
See application file for complete search history.

(56) References Cited

U.S. PATENT DOCUMENTS

| | | | |
|---|---|---|---|
| 2,275,154 A | 3/1942 | Merrill et al. | |
| 2,609,347 A | 9/1952 | Wilson | |
| 3,663,470 A | 5/1972 | Nishimura et al. | |
| 3,737,398 A | 6/1973 | Yamaguchi | |
| 3,957,933 A | 5/1976 | Egli et al. | |
| 4,025,686 A | 5/1977 | Zion | |
| 4,034,759 A | 7/1977 | Haerr | |
| 4,055,377 A | 10/1977 | Erickson et al. | |

(Continued)

FOREIGN PATENT DOCUMENTS

DE      3834705      4/1990

(Continued)

OTHER PUBLICATIONS

Abbara et al., "Transcervical Expulsion of a Fibroid as a Result of Uterine Artery Embolization for Leiomyomata", *JVIR*, vol. 10, No. 4, pp. 409-411, 1999.

(Continued)

*Primary Examiner*—Bruce E Snow
(74) *Attorney, Agent, or Firm*—Fish & Richardson P.C.

(57) ABSTRACT

A method of treating tissue includes placing substantially spherical polymer particles in the tissue. The particles include an interior region having relatively large pores and a first region substantially surrounding the interior having fewer relatively large pores than the interior region.

26 Claims, 13 Drawing Sheets

U.S. PATENT DOCUMENTS

| | | | |
|---|---|---|---|
| 4,076,640 A | 2/1978 | Forgensi et al. |
| 4,094,848 A | 6/1978 | Naito |
| 4,096,230 A | 6/1978 | Haerr |
| 4,098,728 A | 7/1978 | Rosenblatt |
| 4,110,529 A | 8/1978 | Stoy |
| 4,159,719 A | 7/1979 | Haerr |
| 4,191,672 A | 3/1980 | Salome et al. |
| 4,198,318 A | 4/1980 | Stowell et al. |
| 4,243,794 A | 1/1981 | White et al. |
| 4,246,208 A | 1/1981 | Dundas |
| 4,266,030 A | 5/1981 | Tschang et al. |
| 4,268,495 A | 5/1981 | Muxfeldt et al. |
| 4,271,281 A | 6/1981 | Kelley et al. |
| 4,402,319 A | 9/1983 | Handa et al. |
| 4,413,070 A | 11/1983 | Rembaum |
| 4,427,794 A | 1/1984 | Lange et al. |
| 4,428,869 A | 1/1984 | Munteanu et al. |
| 4,429,062 A | 1/1984 | Pasztor et al. |
| 4,442,843 A | 4/1984 | Rasor et al. |
| 4,444,961 A | 4/1984 | Timm |
| 4,452,773 A | 6/1984 | Molday |
| 4,456,693 A | 6/1984 | Welsh |
| 4,459,145 A | 7/1984 | Elsholz |
| 4,472,552 A | 9/1984 | Blouin |
| 4,477,255 A | 10/1984 | Pasztor et al. |
| 4,492,720 A | 1/1985 | Mosier |
| 4,515,906 A | 5/1985 | Friesen et al. |
| 4,522,953 A | 6/1985 | Barby et al. |
| 4,542,178 A | 9/1985 | Zimmermann et al. |
| 4,551,132 A | 11/1985 | Pasztor et al. |
| 4,551,436 A | 11/1985 | Johnson et al. |
| 4,573,967 A | 3/1986 | Hargrove et al. |
| 4,622,362 A | 11/1986 | Rembaum |
| 4,623,706 A | 11/1986 | Timm et al. |
| 4,629,464 A * | 12/1986 | Takata et al. ............. 623/23.61 |
| 4,640,807 A | 2/1987 | Afghan et al. |
| 4,657,756 A | 4/1987 | Rasor et al. |
| 4,661,137 A | 4/1987 | Garnier et al. |
| 4,663,358 A | 5/1987 | Hyon et al. |
| 4,671,954 A | 6/1987 | Goldberg et al. |
| 4,674,480 A | 6/1987 | Lemelson |
| 4,675,113 A | 6/1987 | Graves et al. |
| 4,678,710 A | 7/1987 | Sakimoto et al. |
| 4,678,814 A | 7/1987 | Rembaum |
| 4,680,320 A | 7/1987 | Uku et al. |
| 4,681,119 A | 7/1987 | Rasor et al. |
| 4,695,466 A | 9/1987 | Morishita et al. |
| 4,713,076 A | 12/1987 | Draenert |
| 4,742,086 A | 5/1988 | Masamizu et al. |
| 4,743,507 A | 5/1988 | Franses et al. |
| 4,772,635 A | 9/1988 | Mitschker et al. |
| 4,782,097 A | 11/1988 | Jain et al. |
| 4,789,501 A | 12/1988 | Day et al. |
| 4,793,980 A | 12/1988 | Torobin |
| 4,795,741 A | 1/1989 | Leshchiner et al. |
| 4,801,458 A | 1/1989 | Hidaka et al. |
| 4,804,366 A | 2/1989 | Zdeb et al. |
| 4,819,637 A | 4/1989 | Dormandy, Jr. et al. |
| 4,822,535 A | 4/1989 | Ekman et al. |
| 4,833,237 A | 5/1989 | Kawamura et al. |
| 4,850,978 A | 7/1989 | Dudar et al. |
| 4,859,711 A | 8/1989 | Jain et al. |
| 4,863,972 A | 9/1989 | Itagaki et al. |
| 4,897,255 A | 1/1990 | Fritzberg et al. |
| 4,929,400 A | 5/1990 | Rembaum et al. |
| 4,933,372 A | 6/1990 | Feibush et al. |
| 4,938,967 A | 7/1990 | Newton et al. |
| 4,946,899 A | 8/1990 | Kennedy et al. |
| 4,954,399 A | 9/1990 | Tani et al. |
| 4,981,625 A | 1/1991 | Rhim et al. |
| 4,990,340 A | 2/1991 | Hidaka et al. |
| 4,999,188 A | 3/1991 | Sloldovnik et al. |
| 5,007,940 A | 4/1991 | Berg |
| 5,011,677 A | 4/1991 | Day et al. |
| 5,015,423 A | 5/1991 | Eguchi et al. |
| 5,032,117 A | 7/1991 | Motta |
| 5,034,324 A | 7/1991 | Shinozaki et al. |
| 5,047,438 A | 9/1991 | Feibush et al. |
| 5,079,274 A | 1/1992 | Schneider et al. |
| 5,091,205 A | 2/1992 | Fan |
| 5,106,903 A | 4/1992 | Vanderhoff et al. |
| 5,114,421 A | 5/1992 | Polak |
| 5,116,387 A | 5/1992 | Berg |
| 5,120,349 A | 6/1992 | Stewart et al. |
| 5,125,892 A | 6/1992 | Drudik |
| 5,147,631 A | 9/1992 | Glajch et al. |
| 5,147,937 A | 9/1992 | Frazza et al. |
| 5,149,543 A | 9/1992 | Cohen et al. |
| 5,158,573 A | 10/1992 | Berg |
| 5,171,214 A | 12/1992 | Kolber et al. |
| 5,171,217 A | 12/1992 | March et al. |
| 5,181,921 A | 1/1993 | Makita et al. |
| 5,190,760 A | 3/1993 | Baker |
| 5,190,766 A | 3/1993 | Ishihara |
| 5,192,301 A | 3/1993 | Kamiya et al. |
| 5,202,352 A | 4/1993 | Okada et al. |
| 5,216,096 A | 6/1993 | Hattori et al. |
| 5,253,991 A | 10/1993 | Yokota et al. |
| 5,260,002 A | 11/1993 | Wang |
| 5,262,176 A | 11/1993 | Palmacci et al. |
| 5,263,992 A | 11/1993 | Guire |
| 5,288,763 A | 2/1994 | Li et al. |
| 5,292,814 A | 3/1994 | Bayer et al. |
| 5,302,369 A | 4/1994 | Day et al. |
| 5,314,974 A | 5/1994 | Ito et al. |
| 5,316,774 A | 5/1994 | Eury et al. |
| RE34,640 E | 6/1994 | Kennedy et al. |
| 5,320,639 A | 6/1994 | Rudnick |
| 5,328,936 A | 7/1994 | Leifholtz et al. |
| 5,336,263 A | 8/1994 | Ersek et al. |
| 5,344,452 A | 9/1994 | Lemperle |
| 5,344,867 A | 9/1994 | Morgan et al. |
| 5,354,290 A | 10/1994 | Gross |
| 5,369,133 A | 11/1994 | Ihm et al. |
| 5,369,163 A | 11/1994 | Chiou et al. |
| 5,382,260 A | 1/1995 | Dormandy, Jr. et al. |
| 5,384,124 A | 1/1995 | Courteille et al. |
| 5,397,303 A | 3/1995 | Sancoff et al. |
| 5,398,851 A | 3/1995 | Sancoff et al. |
| 5,403,870 A | 4/1995 | Gross |
| 5,417,982 A | 5/1995 | Modi |
| 5,431,174 A | 7/1995 | Knute |
| 5,435,645 A | 7/1995 | Faccioli et al. |
| 5,443,495 A | 8/1995 | Buscemi et al. |
| 5,456,693 A | 10/1995 | Conston et al. |
| 5,468,801 A | 11/1995 | Antonelli et al. |
| 5,469,854 A | 11/1995 | Unger et al. |
| 5,476,472 A | 12/1995 | Dormandy, Jr. et al. |
| 5,484,584 A | 1/1996 | Wallace et al. |
| 5,490,984 A | 2/1996 | Freed |
| 5,494,682 A | 2/1996 | Cohen et al. |
| 5,494,940 A | 2/1996 | Unger et al. |
| 5,512,604 A | 4/1996 | Demopolis |
| 5,514,090 A | 5/1996 | Kriesel et al. |
| 5,525,334 A | 6/1996 | Ito et al. |
| 5,534,589 A | 7/1996 | Hager et al. |
| 5,541,031 A | 7/1996 | Yamashita et al. |
| 5,542,935 A | 8/1996 | Unger et al. |
| 5,553,741 A | 9/1996 | Sancoff et al. |
| 5,556,391 A | 9/1996 | Cercone et al. |
| 5,556,610 A | 9/1996 | Yan et al. |
| 5,558,255 A | 9/1996 | Sancoff et al. |
| 5,558,822 A | 9/1996 | Gitman et al. |
| 5,558,856 A | 9/1996 | Klaveness et al. |

| | | | | | |
|---|---|---|---|---|---|
| 5,559,266 A | 9/1996 | Klaveness et al. | 5,935,553 A | 8/1999 | Unger et al. |
| 5,567,415 A | 10/1996 | Porter | 5,951,160 A | 9/1999 | Ronk |
| 5,569,193 A | 10/1996 | Hofstetter et al. | 5,957,848 A | 9/1999 | Sutton et al. |
| 5,569,449 A | 10/1996 | Klaveness et al. | 5,959,073 A | 9/1999 | Schlameus et al. |
| 5,569,468 A | 10/1996 | Modi | 6,003,566 A | 12/1999 | Thibault et al. |
| 5,571,182 A | 11/1996 | Ersek et al. | 6,015,546 A | 1/2000 | Sutton et al. |
| 5,580,575 A | 12/1996 | Unger et al. | 6,027,472 A | 2/2000 | Kriesel et al. |
| 5,583,162 A | 12/1996 | Li et al. | 6,028,066 A | 2/2000 | Unger |
| 5,585,112 A | 12/1996 | Unger et al. | 6,047,861 A | 4/2000 | Vidal et al. |
| 5,595,821 A | 1/1997 | Hager et al. | 6,048,908 A | 4/2000 | Kitagawa |
| 5,622,657 A | 4/1997 | Takada et al. | 6,051,247 A | 4/2000 | Hench et al. |
| 5,624,685 A | 4/1997 | Takahashi et al. | 6,056,721 A | 5/2000 | Shulze |
| 5,635,215 A | 6/1997 | Boschetti et al. | 6,056,844 A | 5/2000 | Guiles et al. |
| 5,637,087 A | 6/1997 | O'Neil et al. | 6,059,766 A | 5/2000 | Greff |
| 5,639,710 A | 6/1997 | Lo et al. | 6,063,068 A | 5/2000 | Fowles et al. |
| 5,648,095 A | 7/1997 | Illum et al. | 6,071,495 A | 6/2000 | Unger et al. |
| 5,648,100 A | 7/1997 | Boschetti et al. | 6,071,497 A | 6/2000 | Steiner et al. |
| 5,650,116 A | 7/1997 | Thompson | 6,073,759 A | 6/2000 | Lamborne et al. |
| 5,651,990 A | 7/1997 | Takada et al. | 6,090,925 A | 7/2000 | Woiszwillo et al. |
| 5,653,922 A | 8/1997 | Li et al. | 6,096,344 A | 8/2000 | Liu et al. |
| 5,657,756 A | 8/1997 | Vrba | 6,099,864 A | 8/2000 | Morrison et al. |
| 5,681,576 A | 10/1997 | Henry | 6,100,306 A | 8/2000 | Li et al. |
| 5,695,480 A | 12/1997 | Evans et al. | 6,139,963 A | 10/2000 | Fujii et al. |
| 5,695,740 A | 12/1997 | Porter | 6,149,623 A | 11/2000 | Reynolds |
| 5,698,271 A | 12/1997 | Liberti et al. | 6,160,084 A | 12/2000 | Langer et al. |
| 5,701,899 A | 12/1997 | Porter | 6,162,377 A | 12/2000 | Ghosh et al. |
| 5,715,824 A | 2/1998 | Unger et al. | 6,165,193 A | 12/2000 | Greene, Jr. et al. |
| 5,716,981 A | 2/1998 | Hunter et al. | 6,179,817 B1 | 1/2001 | Zhong |
| 5,718,884 A | 2/1998 | Klaveness et al. | 6,191,193 B1 | 2/2001 | Lee et al. |
| 5,723,269 A | 3/1998 | Akagi et al. | 6,214,331 B1 | 4/2001 | Vanderhoff et al. |
| 5,725,534 A | 3/1998 | Rasmussen | 6,214,384 B1 | 4/2001 | Pallado et al. |
| 5,733,925 A | 3/1998 | Kunz et al. | 6,224,630 B1 | 5/2001 | Bao et al. |
| 5,741,331 A | 4/1998 | Pinchuk | 6,224,794 B1 | 5/2001 | Amsden et al. |
| 5,746,734 A | 5/1998 | Dormandy, Jr. et al. | 6,235,224 B1 | 5/2001 | Mathiowitz et al. |
| 5,752,974 A | 5/1998 | Rhee et al. | 6,238,403 B1 | 5/2001 | Greene, Jr. et al. |
| 5,756,127 A | 5/1998 | Grisoni et al. | 6,245,090 B1 | 6/2001 | Gilson et al. |
| 5,760,097 A | 6/1998 | Li et al. | 6,251,661 B1 | 6/2001 | Urabe et al. |
| 5,766,147 A | 6/1998 | Sancoff et al. | 6,258,338 B1 | 7/2001 | Gray |
| 5,770,222 A | 6/1998 | Unger et al. | 6,261,585 B1 | 7/2001 | Sefton et al. |
| 5,779,668 A | 7/1998 | Grabenkort | 6,264,861 B1 | 7/2001 | Tavernier et al. |
| 5,785,642 A | 7/1998 | Wallace et al. | 6,267,154 B1 | 7/2001 | Felicelli et al. |
| 5,785,682 A | 7/1998 | Grabenkort | 6,268,053 B1 | 7/2001 | Woiszwillo et al. |
| 5,792,478 A | 8/1998 | Lawin et al. | 6,277,392 B1 | 8/2001 | Klein |
| 5,795,562 A | 8/1998 | Klaveness et al. | 6,280,457 B1 | 8/2001 | Wallace et al. |
| 5,797,953 A | 8/1998 | Tekulve | 6,291,605 B1 | 9/2001 | Freeman et al. |
| 5,807,323 A | 9/1998 | Kriesel et al. | 6,296,604 B1 | 10/2001 | Garibaldi et al. |
| 5,813,411 A | 9/1998 | Van Bladel et al. | 6,296,622 B1 | 10/2001 | Kurz et al. |
| 5,823,198 A | 10/1998 | Jones et al. | 6,296,632 B1 | 10/2001 | Luscher et al. |
| 5,827,502 A | 10/1998 | Klaveness et al. | 6,306,418 B1 | 10/2001 | Bley |
| 5,827,531 A | 10/1998 | Morrison et al. | 6,306,419 B1 | 10/2001 | Vachon et al. |
| 5,830,178 A | 11/1998 | Jones et al. | 6,306,425 B1 | 10/2001 | Tice et al. |
| 5,833,361 A | 11/1998 | Funk | 6,306,427 B1 | 10/2001 | Annonier et al. |
| 5,840,387 A | 11/1998 | Berlowitz-Tarrant et al. | 6,312,407 B1 | 11/2001 | Zadno-Azizi et al. |
| 5,846,518 A | 12/1998 | Yan et al. | 6,312,942 B1 | 11/2001 | Plüss-Wenzinger et al. |
| 5,853,752 A | 12/1998 | Unger et al. | 6,315,709 B1 | 11/2001 | Garibaldi et al. |
| 5,855,615 A | 1/1999 | Bley et al. | 6,335,384 B1 | 1/2002 | Evans et al. |
| 5,863,957 A | 1/1999 | Li et al. | 6,344,182 B1 | 2/2002 | Sutton et al. |
| 5,876,372 A | 3/1999 | Grabenkort et al. | 6,355,275 B1 | 3/2002 | Klein |
| 5,877,224 A | 3/1999 | Brocchini et al. | 6,364,823 B1 | 4/2002 | Garibaldi et al. |
| 5,885,216 A | 3/1999 | Evans, III et al. | 6,368,658 B1 | 4/2002 | Schwarz et al. |
| 5,885,547 A | 3/1999 | Gray | 6,379,373 B1 | 4/2002 | Sawhney et al. |
| 5,888,546 A | 3/1999 | Ji et al. | 6,388,043 B1 | 5/2002 | Langer et al. |
| 5,888,930 A | 3/1999 | Smith et al. | 6,394,965 B1 | 5/2002 | Klein |
| 5,891,155 A | 4/1999 | Irie | 6,423,332 B1 | 7/2002 | Huxel et al. |
| 5,894,022 A | 4/1999 | Ji et al. | 6,432,437 B1 | 8/2002 | Hubbard |
| 5,895,398 A | 4/1999 | Wensel et al. | 6,436,112 B2 | 8/2002 | Wensel et al. |
| 5,895,411 A | 4/1999 | Irie | 6,443,941 B1 | 9/2002 | Slepian et al. |
| 5,899,877 A | 5/1999 | Leibitzki et al. | 6,458,296 B1 | 10/2002 | Heinzen et al. |
| 5,902,832 A | 5/1999 | Van Bladel et al. | 6,476,069 B2 | 11/2002 | Krall et al. |
| 5,902,834 A | 5/1999 | Porrvik | 6,495,155 B1 | 12/2002 | Tice et al. |
| 5,922,025 A | 7/1999 | Hubbard | 6,544,503 B1 | 4/2003 | Vanderhoff et al. |
| 5,922,304 A | 7/1999 | Unger | 6,544,544 B2 | 4/2003 | Hunter et al. |
| 5,928,626 A | 7/1999 | Klaveness et al. | 6,545,097 B2 | 4/2003 | Pinchuk et al. |

| | | |
|---|---|---|
| 6,575,896 B2 | 6/2003 | Silverman et al. |
| 6,602,261 B2 | 8/2003 | Greene, Jr. et al. |
| 6,602,524 B2 | 8/2003 | Batich et al. |
| 6,605,111 B2 | 8/2003 | Bose et al. |
| 6,629,947 B1 | 10/2003 | Sahatjian et al. |
| 6,632,531 B2 | 10/2003 | Blankenship |
| 6,652,883 B2 | 11/2003 | Goupil et al. |
| 6,680,046 B1 | 1/2004 | Boschetti |
| 6,699,222 B1 | 3/2004 | Jones et al. |
| 7,053,134 B2 | 5/2006 | Baldwin et al. |
| 7,094,369 B2 | 8/2006 | Buiser et al. |
| 2001/0001835 A1 | 5/2001 | Greene, Jr. et al. |
| 2001/0016210 A1 | 8/2001 | Mathiowitz et al. |
| 2001/0036451 A1 | 11/2001 | Goupil et al. |
| 2001/0051670 A1 | 12/2001 | Goupil et al. |
| 2002/0054912 A1 | 5/2002 | Kim et al. |
| 2002/0061954 A1 | 5/2002 | Davis et al. |
| 2002/0160109 A1 | 10/2002 | Yeo et al. |
| 2002/0182190 A1 | 12/2002 | Naimark et al. |
| 2002/0197208 A1 | 12/2002 | Ruys et al. |
| 2003/0007928 A1 | 1/2003 | Gray |
| 2003/0032935 A1 | 2/2003 | Damiano et al. |
| 2003/0108614 A1 | 6/2003 | Volkonsky et al. |
| 2003/0185895 A1 | 10/2003 | Lanphere et al. |
| 2003/0185896 A1 | 10/2003 | Buiser et al. |
| 2003/0187320 A1 | 10/2003 | Freyman |
| 2003/0194390 A1 | 10/2003 | Krall et al. |
| 2003/0206864 A1 | 11/2003 | Mangin |
| 2003/0215519 A1 | 11/2003 | Schwarz et al. |
| 2004/0076582 A1 | 4/2004 | Dimatteo et al. |
| 2004/0091543 A1 | 5/2004 | Bell et al. |
| 2004/0092883 A1 | 5/2004 | Casey, III et al. |
| 2004/0096662 A1 | 5/2004 | Lanphere et al. |
| 2004/0101564 A1 | 5/2004 | Rioux et al. |
| 2004/0186377 A1 | 9/2004 | Zhong et al. |
| 2005/0025800 A1 | 2/2005 | Tan |
| 2005/0037047 A1 | 2/2005 | Song |
| 2005/0095428 A1 | 5/2005 | Dicarlo et al. |
| 2005/0129775 A1 | 6/2005 | Lanphere et al. |
| 2005/0196449 A1 | 9/2005 | Dicarlo et al. |
| 2005/0208107 A1 | 9/2005 | Helmus et al. |
| 2005/0226935 A1 | 10/2005 | Kamath et al. |
| 2005/0238870 A1 | 10/2005 | Buiser et al. |
| 2005/0263916 A1 | 12/2005 | Lanphere et al. |
| 2006/0045900 A1 | 3/2006 | Richard et al. |
| 2006/0116711 A1 | 6/2006 | Elliott et al. |
| 2006/0173090 A1 | 8/2006 | Baldwin et al. |
| 2006/0199009 A1 | 9/2006 | Anderson et al. |
| 2006/0199010 A1 | 9/2006 | DiCarlo et al. |
| 2006/0210710 A1 | 9/2006 | Buiser et al. |
| 2006/0247610 A1 | 11/2006 | Lanphere et al. |
| 2006/0292300 A1 | 12/2006 | Tan |
| 2007/0004973 A1 | 1/2007 | Tan |

FOREIGN PATENT DOCUMENTS

| | | |
|---|---|---|
| DE | 94 14 868.6 | 12/1994 |
| DE | 297 24 255 U1 | 10/2000 |
| DE | 100 26 620 | 3/2002 |
| EP | 0 067 459 | 12/1982 |
| EP | 0 122 624 | 10/1984 |
| EP | 0 123 235 | 10/1984 |
| EP | 0 243 165 | 10/1987 |
| EP | 0 294 206 | 12/1988 |
| EP | 0 402 031 | 12/1990 |
| EP | 0 422 258 | 4/1991 |
| EP | 0 458 079 | 11/1991 |
| EP | 0 458 745 | 11/1991 |
| EP | 0 470 569 | 2/1992 |
| EP | 0 547 530 | 6/1993 |
| EP | 0 600 529 | 6/1994 |
| EP | 0 623 012 | 11/1994 |
| EP | 0 706 376 | 4/1996 |
| EP | 0 730 847 | 9/1996 |
| EP | 0 744 940 | 12/1996 |
| EP | 0 764 047 | 3/1997 |
| EP | 0 797 988 | 10/1997 |
| EP | 0 993 337 | 4/2000 |
| ES | 2 096 521 | 3/1997 |
| JP | 59-196738 | 11/1984 |
| JP | 62-45637 | 2/1987 |
| JP | 4-74117 | 3/1992 |
| JP | 6-57012 | 3/1994 |
| JP | 9-110678 | 4/1997 |
| JP | 9-165328 | 6/1997 |
| JP | 9-316271 | 12/1997 |
| JP | 10-130329 | 5/1998 |
| JP | 2000189511 | 7/2000 |
| JP | 2001079011 | 3/2001 |
| JP | 2002-017848 | 1/2002 |
| NZ | 255409 | 2/1997 |
| NZ | 517377 | 8/2003 |
| TW | 421658 | 2/2001 |
| WO | WO 91/12823 | 5/1991 |
| WO | WO 92/21327 | 12/1992 |
| WO | WO 93/00063 | 1/1993 |
| WO | WO 93/19702 | 10/1993 |
| WO | WO 94/10936 | 5/1994 |
| WO | WO 95/03036 | 2/1995 |
| WO | WO 95/22318 | 8/1995 |
| WO | WO 95/33553 | 12/1995 |
| WO | WO 96/37165 | 11/1996 |
| WO | WO 96/39464 | 12/1996 |
| WO | WO 98/04616 | 2/1998 |
| WO | WO 98/10798 | 3/1998 |
| WO | WO 98/26737 | 6/1998 |
| WO | WO 98/47532 | 10/1998 |
| WO | WO 99/00187 | 1/1999 |
| WO | WO 99/12577 | 3/1999 |
| WO | WO 99/43380 | 9/1999 |
| WO | WO 99/51278 | 10/1999 |
| WO | WO 99/57176 | 11/1999 |
| WO | WO 00/23054 | 4/2000 |
| WO | WO 00/032112 | 6/2000 |
| WO | WO 00/40259 | 7/2000 |
| WO | WO 00/71196 | 11/2000 |
| WO | WO 00/74633 | 12/2000 |
| WO | WO 01/12359 | 2/2001 |
| WO | WO 01/66016 | 9/2001 |
| WO | WO 01/70291 | 9/2001 |
| WO | WO 01/72281 | 10/2001 |
| WO | WO 01/76845 | 10/2001 |
| WO | WO 01/93920 | 12/2001 |
| WO | WO 02/11696 | 2/2002 |
| WO | WO 02/34298 | 5/2002 |
| WO | WO 02/34299 | 5/2002 |
| WO | WO 02/34300 | 5/2002 |
| WO | WO 02/43580 | 6/2002 |
| WO | WO 03/016364 | 2/2003 |
| WO | WO 03/051451 | 6/2003 |
| WO | WO 03/082359 | 10/2003 |
| WO | WO 2004/019999 | 3/2004 |
| WO | WO 2004/073688 | 9/2004 |
| WO | WO 2004/075989 | 9/2004 |

OTHER PUBLICATIONS

Abrahams, J.M. et al., "Topic Review: Surface Modifications Enhancing Biological Activity of Guglielmi Detachable Coils in Treating Intracranial Aneurysms", *Surg. Neurol.* 54:34-41, 2000.

Abrahams, J.M. et al., "Delivery of Human Vascular Endothelial Growth Factor with Platinum Coils Enhances Wall Thickening and Coil Impregnation in a Rat Aneurysm Model", *AJNR Am. J. Neuroradiol.* 22:1410-1417, Aug. 2001.

Abuja, A.A., "Platinum Coil Coatings to Increase Thrombogenicity: A Preliminary Study in Rabbits", *AJNR Am. J. Neuroradiol.* 14:794-798; Jul./Aug. 1993.

Antibody Labeling, http://www.altcorp.com/AffinityLabeling/ablaeling.htm, pp. 1-6, May 20, 2003.

Bachtsi, A.R. et al., "An Experimental Investigation of Enzyme Release from Poly(vinyl alcohol) crosslinked Microspheres", *J. Microencapsulation*, vol. 12, No. 1, pp. 23-35; 1995.

Barr, J.D. et al., "Polyvinyl Alcohol Foam Particles Sizes and Concentrations Injectable through Microcatheters", *JVIR*, vol. 9, No. 1, pp. 113-118; 1998.

Barton, P. et al., "Embolization of Bone Metastases," *Journal of Vascular and Interventional Radiology*, 7 (1):81-88 (Jan.-Feb. 1996).

Battinelli, L. et al., "New Class of Poly(vinyl alcohol) Polymrs as Column-Chromatography Stationary Phases for Candida Rugosa Lipase Isoforms Separation", *J. Chromatogr A*, vol. 753, No. 1, pp. 47-55; 1996.

Beaujeux, R. et al., "Trisacryl Gelatin Microspheres for Therapeutic Embolization, H: Preliminary Clinical Evaluation in Tumors and Arteriovenous Malformations," *AJNR Am. J. Neuroradiol.*, 17:541-548, Mar. 1996.

Berenstein, A. et al., "Catheter and Material Selection for Transarterial Embolization: Technical Considerations. II. Materials.", *Radiology*, vol. 132, No. 3, pp. 631-639; 1979.

Berenstein, A. et al., "Microembolization Techniques of Vascular Occlusion: Radiologic, Patohologic, and Clinical Correlation", *AJNR Am I Neuroradiol*, vol. 2, No. 3, pp. 261-267; 1981.

Berkowitz, R.P. et al., "Vaginal Expulsion of Submucosal Fibroids After Uterine Artery Embolization", *Journal of Reproductive Medicine*, vol. 44, No. 4, pp. 373-376; Apr. 1999 http://www.reproductivemedicine.com.

Bourke et al., "Protein Drug Release from Photocrosslinked Poly(vinyl alcohol) Hydrogels," *Society for Biomaterials 28th Annual Meeting Transactions*, p. 144 (2002).

Bradley, E.A. et al., "Transcatheter Uterine Artery Embolisation to Treat Large Uterine Fibroids", *British Journal of Obstetrics and Gynaecology*, vol. 105, pp. 235-240; Feb. 1998.

Brockmann, J. et al., "Radiolabeling of p-Bz-DOTA-CD-11c antibody with $^{88}$Y: Conjugation, Labeling, Biodistribution studies", 2 pages, 2000 http://www.kernchemie.uni-mainz.de/downloads/jb2000/b14_brockmann pdf.

Bruix, J. et al., "Transarterial Embolization Versus Symptomatic Treatment in Patients With Advanced Hepatocellular Carcinoma: Results of a Randomized, Controlled Trial in a Single Institution", *Hepatology*, Jun. 1998, vol. 27, No. 6, pp. 1578-1583, http://www.hepatitis-central.com/hcv/hcc/embolization/references.html.

Buhle, Jr. EL, "Re: Re: Hepatic Arterial Embolization", *UCLA Medicine Online*, Mar. 10, 1996, http://www.meds.com/archive/mol-cancer/1996/msg00128.html, 2 pages.

Burczak, et al., "Long-term in vivo performance and biocompatibility of poly (vinyl alcohol) hydrogel macrocapsules for hybrid-type artificial pancreas", *Biomaterials*, vol. 17, No. 24, pp. 2351-2356, 1996.

Burczak, et al., "Polymeric materials for biomedical purposes obtained by radiation methods. V. hybrid artificial pancreas", *Polim Med*, vol. 24, No. 1-2, pp. 45-55, 1994 (English Summary included).

Capozza et al., "Endoscopic treatment of vesico-ureteric reflux and urinary incontinence: technical problems in the paediatric patient," *British Journal of Urology*, 75(4):538-542 (Apr. 1995).

Carroll, B.A. et al., "Microbubbles as Ultrasonic Contrast Agents", *Investigative Radiology*, vol. 14, No. 3, p. 374, Supplement to May-Jun. 1979.

Carroll, B.A. et al., "Gelatin Encapsulated Nitrogen Microbubbles as Ultrasonic Contrast Agents", *Journal of Clinical and Laboratory Research*, vol. 15, No. 1, pp. 260-266, Feb. 1980.

Carstensen, E.L. et al., "Determination of the Acoustic Properties of Blood and its Components", *Journal of Acoustical Society of America*, vol. 25, No. 2, pp. 286-289, Mar. 1953.

Choe, et al., "An experimental study of embolic effect according to infusion rate and concentration of suspension in transarterial particulate embolization", *Invest Radiol*, vol. 32, No. 5, pp. 260-270, 1997.

Chuang et al., "Experimental Canine Hepatic Artery Embolization with Polyvinyl Alcohol Foam Particles", *Departments of Diagnostic Radiology and Veterinary Medicine*, The University of Texas, M.D. Anderson Hospital and Tumor Institute at Houston, Texas, pp. 21-25, Oct. 1982.

Cirkel, U. et al., "Experience with Leuprorelin Acetate Depot in the Treatment of Fibroids: A German Multicentre Study", *Clinical Therapeutics*, vol. 14, Suppl. A, 1992.

Clarian Health Methodist—Indiana Lions Gamma Knife Center, "Arteriovenous Malformation," http://www.clarian.com/tyhealth/gammaknife/cond_arter.asp, 4 pages, Last Updated on Mar. 20, 2000.

Colombo M, "Treatment of Hepatocellular Carcinoma", *Journal of Viral Hepatitis*, 4(Suppl. 1):125-130 (1997), http://home.texoma.net/~moreland/stats/hcc-9.html.

Concentric Medical, Inc.—Product Information (3 pages), 2002.

Cruise et al., "In Vitro and in Vivo Characterization of a Hydrogel-Based Aneurysm Embolization System," *Society for Biomaterials 28th Annual Meeting Transactions*, p. 203 (2002).

Deasy, P. B., *"Microencapsulation and Related Drug Processes"*, New York, Ny, Marcel Dekker, Inc., 345 pages, 1984 (Table of Contents only).

de Gast, A.N. et al., "Transforming Growth Factor β-coated Platinum Coils for Endovascular Treatment of Aneurysms: An Animal Study", *Neurosurgery*, vol. 49, No. 3, pp. 690-696, Sep. 2001.

Derdeyn, et al., "Collagen-coated acrylic microspheres for embolotherapy: in vivo and in vitro characteristics", *American Journal of Neuroradiology*, vol. 18, No. 4, pp. 647-653, 1997.

Derdeyn, et al., "Polyvinyl alcohol particle size and suspension characteristics", *American Journal of Neuroradiology*, vol. 16, pp. 1335-1343, 1995.

DiLuccio et al., "Sustained-Release Oral Delivery of Theophylline by Use of Polyvinyl Alcohol and Polyvinyl Alcohol-Methyl Acrylate Polymers", Journal of Pharmaceutical Sciences, vol. 83, No. 1, pp. 104-106, Jan. 1994.

Duckwiler et al., "Catheters, embolic agents spark neurointervention," *Diagnostic Imaging*, 16(5):66-72 (May 1994).

Ersek et al., "Bioplastique: A New Textured Copolymer Microparticle Promises Permanence in Soft-Tissue Augmentation," *Plastic and Reconstructive Surgery*, 87(4):693-702 (Apr. 1991).

Eskridge, "Interventional Neuroradiology," *Radiology*, 172:991-1006 (Nov. 1989).

Feldman, L. et al., "Transcatheter Vessel Occlusion- Angiographic Results Versus Clinical Success", *Radiology*, vol. 147, pp. 1-5, Apr. 1983.

Ferrofluids, Physical Properties and Applications Ferrofluidics Corp., Nashua, NH, 5 pages, 1986.

FeRx Incorporated, FERX Profile http://www.biotechshares.com/FERX.htm, 4 pages (Retrieved from the internet on Jun. 26, 2003).

"Fibroid Treatment Collective—Fibroid Embolization," 2 pages, http://www.fibroids.org.

Fritzsch, T. et al., "SH U 508, A Transpulmonary Echocontrast Agent", Investigative Radiology, vol. 25, Supplement 1, pp. S160-S161, Sep. 1990.

Fujimoto, S. et al., "Biodegradable Mitomycin C Microspheres Given Intra-Arterially for Inoperable Hepatic Cancer", *Cancer*, vol. 56, pp. 2404-2410, 1985.

Gander, et al., "Effect of polymeric network structure on drug release from cross-linked poly(vinyl alcohol) micromatrices", *Pharm Res*, vol. 6, No. 7, pp. 578-584, 1989.

Germano, et al., "Histopathological follow-up study of 66 cerebral arteriovenous malformations after therapeutic embolization with polyvinyl alcohol", *J Neurosurg*, vol. 76, No. 4, pp. 607-614, 1992.

Geschwind et al., "Chemoembolization of Liver Tumor in a Rabbit Model: Assessment of Tumor Cell Death with Diffusion-Weighted MR Imaging and Histologic Analysis", *Journal of Vascular and Interventional Radiology*, vol. 11, No. 10, pp. 1244-1255, Dec. 2000.

Gilbert, W.M. et al., "Angiographic Embolization in the Management of Hemorrhagic Complications of Pregnancy", *American Journal of Obstetrics and Gynecology*, vol. 166, No. 2, pp. 493-497, Feb. 1992.

Gohel, et al., "Formulation design and optimization of modified-release microspheres of diclofenac sodium", *Drug Dev Ind Pharm*, vol. 25, No. 2, pp. 247-251, 1999.

Goldberg, B.B., "Ultrasonic Cholangiography", *Radiology*, vol. 118, pp. 401-404, Feb. 1976.

Goodwin, et al., "Overview of embolic agents and their indications", *Eleventh Annual International Symposium on Endovascular Therapy*, pp. 303-306, 1999.

Goodwin, et al., "Preliminary experience with uterine artery embolization for uterine fibroids", *Journal of Vascular and Interventional Radiology*, vol. 8, No. 4, pp. 517-526, 1997.

Gramiak et al., "Echocardiography of the Aortic Root," *Investigative Radiology*, 3(5):356-366 (Sep.-Oct. 1968).

Gramiak, R. et al., "Ultrasound Cardiography: Contrast Studies in Anatomy and Function", *Radiology*, vol. 92, No. 5, pp. 939-948, Apr. 1969.

Grandfils, et al., "Preparation of poly (D,L) lactide microspheres by emulsion solvent evaporation, and their clinical implications as a convenient embolic material", *J Biomed Mater Res*, vol. 26, No. 4, pp. 467-479, 1992.

Greenwood, L.H. et al., "Obstetric and Nonmalignant Gynecologic Bleeding: Treatment with Angiographic Embolization", *Radiology*, vol. 164, No. 1, pp. 155-159, Jul. 1987.

Gupta et al., "Plasma-induced graft polymerization of acrylic acid onto poly(ethylene terephthalate) films: characterization and human smooth muscle cell growth on grafted films," *Biomaterials*, 23:863-871 (2002).

Halstenberg et al., "Biologically Engineered Protein-*graft*-Poly(ethylene glycol) Hydrogels: A Cell Adhesive and Plasmin-Degradable Biosynthetic Material for Tissue Repair," *Biomacromolecules*, 3(4):710-723 (2002).

Hamada et al., "Embolization with Cellulose Porous Beads, II: Clinical Trial," *AJNR Am. J. Neuroradiol.*,17:1901-1906 (Nov. 1996).

Hirano et al., "Transcutaneous Intrafold Injection For Unilateral Vocal Fold Paralysis: Functional Results," *Ann. Otot Rhinol Laryngol.*, 99(8):598-604 (Aug. 1990).

Horak et al., "Hydrogels in endovascular embolization. I. Spherical particles of poly (2-hydroxyethyl methacrylate) and their medicobiological properties", *Biomaterials*, 7(3):188-192 (May 1986).

Horak et al., "Hydrogels in endovascular embolization. II. Clinical use of spherical particles", *Biomaterials*, 7(6):467-470 (Nov. 1986).

Huang et al., "Percutaneous endovascular embolization of intracerebral arteriovenous malformations. Experience in 72 cases", *Chin Med J*, vol. 108, No. 6, pp. 413-419, 1995.

"Injectable Tissue Implant Could Repair Ravages of Surgery", Clemson University, Biotech Week, Oct. 22, 2003, p. 117.

Jack, et al., "Radiolabeled polyvinyl alcohol particles: a potential agent to monitor embolization procedures", *Int J Rad Appl Instrum B*, vol. 13, No. 3, pp. 235-243, 1986.

Jiaqi, Y. et al., "A New Embolic Material: Super Absorbent Polymer (SAP) Microsphere and Its Embolic Effects," *Nippon Acta Radiologica*, 56:19-24 (1996) (English Abstract included).

Jones, S.K. et al., "Experimental Examination of a Targeted Hyperthermia System Using Inductively Heated Ferromagnetic Microspheres in Rabbit Kidney", *Phys. Med. Biol.*, vol. 46, No. 2, pp. 385-398, Feb. 2001, www.iop.org/Journals/pb.

Joy C, et al., "Use of Preoperative Embolization in the Treatment of Vascular Metastatic Lesions of the Spine," http://www.aaos.org/wordhtml/anmeet91/scipro/ppr472.htm, Mar. 12, 1991.

Jung et al., "Sulfobutylated poly(vinyl alcohol)-graft-poly(lactide-co-glycolide)s facilitate the preparation of small negatively charged biodegradable nanospheres," *Journal of Controlled Release*, 67:157-169 (2000).

Kai, et al., "The utility of the microcrystalline cellulose sphere as a particulate embolic agent: an experimental study", *American Journal of Radiology*, vol. 21, No. 6, pp. 1160-1163, 2000.

Kallmes, D.E. et al., "In Vitro Proliferation and Adhesion of Basic Fibroblast Growth Factor-producing Fibroblasts on Platinum Coils", *Radiology*, vol. 206, No. 1, pp. 237-243, Jan. 1998.

Kan, et al., "In vivo microscopy of the liver after injection of lipiodol into the hepatic artery and portal vein in the rat", *Acta Radiologica*, vol. 30, pp. 419-425, 1989.

Kerber, C., "Balloon Catheter with a Calibrated Leak", *Radiology*, vol. 120, pp. 547-550, Sep. 1976.

Kerber et al., "Polyvinyl Alcohol Foam: Prepackaged Emboli for Therapeutic Embolization", *American Journal Roentgenol*, vol. 130, pp. 1193-1194, Jun. 1978.

Kerber, "Flow-Controlled Therapeutic Embolization: A Physiologic and Safe Technique", *AJR*, vol. 134, pp. 557-561, Mar. 1980.

Khankan et al., "Embolic Effects of Superabsorbent Polymer Microspheres in Rabbit Renal Model: Comparison with Tris-acryl Gelatin Microspheres and Polyvinyl Alcohol," *Radiation Medicine*, 22(6):384-390 (2004).

Kim, et al., "Composite poly(vinyl alcohol) beads for controlled drug delivery", *Pharm Res*, vol. 9. No. 1, pp. 10-16, 1992.

Kim et al., "Hollow Silica Spheres of Controlled Size and Porosity by Sol-Gel Processing," *J. Am. Ceram. Soc.*, 74(8):1987-1992 (Aug. 1991).

Kim et al., "Poly(vinyl alcohol) beads with core-shell structure for drug delivery," *Cosmetic and Pharmaceutical Applications of Polymers*, Plenum Press, New York, pp. 209-214 (1991).

Kim et al., "Suspension polymerized poly(vinyl alcohol) beads for drug delivery," *Polymeric Materials: Science and Engineering, Proceedings of the ACS Division of Polymeric Materials: Science and Engineering*, 63:64-67 (1990).

Krinick et al., "A polymeric drug delivery system for the simultaneous delivery of drugs activatable by enzymes and/or light," *J. Biomater. Sci. Polymer Edn*, 5(4):303-324 (1994).

Kuhn, R. et al., "Embolic Occlusion of the Blood Supply to Uterine Myomas: Report of 2 Cases", *Aust. NZ. J. Obstet. Gynaecol.*, vol. 39, No. 1, pp. 120-122, Feb. 1999.

Kurata, et al., "Preoperative embolization for meningiomas using PVA Particles", *No Shinkei Geka*, vol. 20, No. 4, pp. 367-373, 1992 (English Abstract Included).

Kurbatova, G.T. et al., "Magnetically-guided Anesthetics Based on Highly Dispersed Iron Powders Coated by Polyacrylamide", *Biofizika*, vol. 47, No. 2, pp. 331-337, Mar.-Apr. 2002 http://intapp.medscape.com/px/medlineapp (English Abstract included).

Kurosaki et al., "Evaluation of PVA-Gel Spheres as GI-Transit Time Controlling Oral Drug Delivery System", *Proceedings of the 19th International Symposium on Controlled Release of Bioactive Materials*, Orlando, Florida, pp. 273-274, Jul. 26-31, 1992.

Kusano, et al., "Low-dose particulate polyvinylalcohol embolization in massive small artery intenstinal hemorrahage. Experimental and clinical results", *Invest Radiol*, vol. 22, No. 5, pp. 388-392, 1987.

Labarre et al., "Complement activation by substituted polyacrylamide hydrogels for embolisation and implantation", *Biomaterials*, vol. 23, pp. 2319-2327, 2002.

Lammer, et al., "Transcatheteral embolization with polyvinyl alcohol—technic and experimental studies", *Rontgenblatter*, vol. 36, No. 1, pp. 10-14, 1983 (English Abstract included).

Latchaw et al., "Polyvinyl Foam Embolization of Vascular and Neoplastic Lesions of the Head, Neck, and Spine", *Radiology*, vol. 131, pp. 669-679, Jun. 1979.

Laurent, "Materials and biomaterials for interventional radiology," *Biomed. & Pharmacother.*, 52:76-88 (1998).

Lemperle et al., "PMMA Microspheres for Intradermal Implantation: Part I. Animal Research," *Annals of Plastic Surgery*, 26(1):56-63 (Jan. 1991).

Lendlein, A. et al., "Biodegradable, Elastic Shape-Memory Polymers for Potential Biomedical Applications", *Science*, vol. 296, pp. 1673-1676, May 31, 2002.

Leung et al., "Determinants of Postembolization Syndrome after Hepatic Chemoembolization", *Journal of Vascular and Interventional Radiology*, vol. 12, No. 3, pp. 320-326, Mar. 2001.

Leventon, William, "Hemocompatible Coatings for Blood-Contacting Devices", *Medical Device & Diagnostic Industry: Coating Technologies—New Methods to Ensure Blood Compatibility*, vol. 25, No. 8, pp. 62-67, Aug. 2003.

Levy et al. "Transcatheter Uterine Artery Embolization for the Treatment of Symptomatic Uterine Fibroid Tumors," *Journal of Women's Imaging*, 2(4):168-175 (2000).

Lipman, "Uterine artery embolization for the treatment of symptomatic uterine fibroids: A review," *Applied Radiology*, 29(7): (Jul. 15-20, 2000).

Lowery, C.L. et al., "Screening Tests for Intrauterine Growth Retardation: A Comparison of Umbilical Artery Doppler to Real-Time Ultrasound", *Echocardiography*, vol. 7, No. 2, pp. 159-164, Mar. 1990.

Marich, K.W. et al., "Real-Time Imaging with a New Ultrasonic Camera: Part I, In Vitro Experimental Studies on Transmission Imaging of Biological Structures", *Journal of Clinical Ultrasound*, vol. 3, No. 1, pp. 5-16, Mar. 1975.

Markoff, et al., "Uterine arteriovenous malformation successfully embolized with a liquid polymer, isobutyl 2-cyanoacrylate", *Am. J. Obstet. Gynecol.*, 155:659-660 (Sep. 1986).

Markus et al., "Experimental Aspects of High-Intensity Transient Signals in the Detection of Emboli," *J. Clin. Ultrasound.*, 23(2):81-87 (Feb. 1995).

Maruhashi, "Modified Polyvinyl Alcohols I and II, " *Polyvinyl Alcohol—Developments*, John Wiley & Sons, Chichester, England, pp. 160-161 and pp. 186-191 (1992).

Marx, W. F. et al., "Endovascular Treatment of Experimental Aneurysms by Use of Biologically Modified Embolic Devices: Coil-mediated Intraaneurysmal Delivery of Fibroblast Tissue Allografts", *AJNR. Am. J. Neuroradiol.*, vol. 22, pp. 323-333, Feb. 2001.

Matsumaru, et al., "Embolic materials for endovascular treatment of cerebral lesions", *J Biomater Sci Polym Ed*, vol. 8, No. 7, pp. 555-569, 1997.

Matsumoto, H. et al., "Basic Fibroblast Growth Factor Released from a Platinum Coil with a Polyvinyl Alcohol Core Enhances Cellular Proliferation and Vascular Wall Thickness: An In Vitro and In Vivo Study", Neurosurgery, vol. 53, No. 2, pp. 402-408, Aug. 2003.

Matsumoto, Y. et al., "Room-Temperature Ferromagnetism in Transparent Transition Metal-Doped Titanium Dioxide", *Science*, vol. 291, pp. 854-856, Feb. 2, 2001 www.sciencemag.org.

Mavligit, G. et al., "Gastrointestinal Leiomyosarcoma Metastatic to the Liver," *Cancer*, 75(8):2083-2088 (Apr. 15, 1995).

McIvor, J. et al., "Pregnancy After Uterine Artery Embolization to Control Haemorrhage from Gestational Trophoblastic Tumour", *British Journal of Radiology*, vol. 69, No. 823, pp. 624-629, Jul. 1996.

MerocelXL Sponge with Hytrol http://www.xomed.com/newproducts/merocelxl/merocelxl_earwick.asp, 3 pages, 2001.

Mid-America Interventional Radiological Society, "New Treatment for Uterine Fibroids Avoids Surgery," http://www.mirs.org/fibroids.htm, 6 pages, Submitted in Oct. 1999.

Moroz, P. et al., "Arterial Embolization Hyperthermia in Porcine Renal Tissue", Journal of Surgical Research, vol. 105, No. 2, pp. 209-214, Jun. 15, 2002.

Moroz, P. et al., "Hepatic Clearance of Arterially Infused Ferromagnetic Particles", *Int. J. Hyperthermia*, vol. 19, No. 1, pp. 23-24, Feb. 2003, http://www.tandf.co.uk/journals.

Nakabayashi, et al., "Evaluation of particulate embolic materials with MR imaging, scanning electron microscopy, and phase-contrast microscopy", *American Journal of Neuroradiology*, vol. 18, No. 3, pp. 485-491, 1997.

Nakstad, et al., "Embolization of intracranial arteriovenous malformations and fistulas with polyvinyl alcohol particles and platinum fibre coils", *Neuroradiology*, vol. 34, No. 4, pp. 348-351, 1992.

Namiki, "Application of Teflon Paste for Urinary Incontinence—Report of 2 Cases," *Uro. Int.*, 39:280-282 (1984).

Nash, et al., "Modifications of polystyrenic matrices for the purification of proteins. II. Effect of the degree of glutaraldehyde-poly(vinyl alcohol) crosslinking on various dye ligand chromatography systems",*J Chromatogr A*, vol. 776, No. 1, pp. 55-63, 1997.

Nikishin LF et al., "Interventional radiology in diffuse toxic goiter", *European Congress of Radiology*, Abstract 9041, 1999, http://www.ecr.org/conferences/ecr1999/sciprg/abs/p090041.htm, 7 pages.

Ophir, et al., "Ultrasonic backscatter from contrast producing collagen microspheres", *Ultrasonic Imaging*, vol. 2, pp. 67-77, 1980.

Orienti et al., "Crosslinked Polyvinylalcohol Hydrogels as Vehicles for Hydrophilic Drugs," *Arch. Pharm. Pharm. Med. Chem.*, 333:421-424 (2000).

Orsini, L. F. et al., "Pelvic Organs in Premenarcheal Girls: Real-Time Ultrasonography", *Radiology*, vol. 153, No. 1, pp. 113-116, Oct. 1984.

Parker, et al., "A particulate contrast agent with potential for ultrasound imaging of liver", *Ultrasound in Medicine and Biology*, vol. 13, No. 9, pp. 555-566, 1987.

Pedley et al., "Hydrogels in Biomedical Applications," *British Polymer Journal*, 12:99-110 (Sep. 1980).

Pesant A.C. et al., "Dural fistulas involving the cavernous sinus: Treatment by embolization—7 cases", *European Congress of Radiology*, Abstract 3-088, 1997, http://www.ecr.org/conferences/ecr1997/sciprg/abs/9703088p.htm, 1 page.

Phillips, D. R. et al., "Experience with Laparoscopic Leiomyoma Coagulation and Concomitant Operative Hysteroscopy", *J. Am. Assoc. Gynecol. Laparosc*, vol. 4, No. 4, pp. 425-533, Aug. 1997.

Pistel et al., "Brush-like branched biodegradable polyesters, part III Protein release from microspheres of poly(vinyl alcohol)-graft-poly(D,L-lactic-co-glycolic acid)," *Journal of Controlled Release*, 73:7-20 (2001).

Politano et al., "Periurethral Teflon Injection for Urinary Incontinence," *The Journal of Urology*, 111:180-183 (1974).

Poppe, W. et al., "Pregnancy after Transcatheter Embolization of a Uterine Arteriovenous Malformation", *Am. J. Obstet. Gynecol.*, vol. 156, No. 5, pp. 1179-1180, May 1987.

Pritchard, et al., "Poly(Vinyl Alcohol): Basic Properties and Uses", London, England: Gordon and Breach Science Publishers, pp. 95-97, 1970.

Progelhof et al., "Table 4.21. Properties of electrical insulating films (101)," *Polymer Engineering Principles: Properties, Processes, and Tests for Design*, Hanser Publishers, Munich, p. 383 (1993).

Purdy, et al., "Arteriovenous malformations of the brain: choosing embolic materials to enhance safety and ease of excision", *J Neurosurg*, vol. 77, No. 2, pp. 217-222, 1992.

PVA Plus, AngioDynamicse Inc., "Reliable PVA Foam Formulated for Consistency and Controlled Delivery—Embolization Particles Ordering Information," www.angiodynamics.com, 2 pages (Aug. 2002).

Quisling, et al., "Histopathology analysis of intraarterial polyvinyl alcohol microemboli in rat cerebral cortex", *American Journal of Neuroradiology*, vol. 5, pp. 101-104, 1984.

Rajan et al., "Sarcomas Metastatic to the Liver: Response and Survial after Cisplatin, Doxorubicin, Mitomycin-C, Ethiodol, and Polyvinyl Alcohol Chemoembolization", *Journal of Vascular and Interventional Radiology*, vol. 12, No. 2, pp. 187-193, Feb. 2001.

Ramos, et al., "Tumor vascular signals in renal masses: detection with Doppler US", *Radiology*, vol. 168, No. 3, pp. 633-637, 1988.

Ravina, J.H. et al., "Advantage of Pre-Operative Embolization of Fibroids: About a Multicentric Set of 31 Cases", *Contracept. Fertil. Sex.*, vol. 23, No. 1, pp. 45-49, Jan. 1995 (English Abstract included).

Ravina, J.H. et al., "Arterial Embolisation to Treat Uterine Myomata",*Lancet*, vol. 346, pp. 671- 674, Sep. 9, 1995.

Ravina, J.H. et al., "Interest of Particulate Arterial Embolization in the Treatment of Some Uterine Myoma", *Bull. Acad. Natle. Med.*, vol. 181, No. 2, pp. 233-246, Feb. 4, 1997 (English Summary included).

Repa, I. et al., "Mortalities Associated with Use of a Commercial Suspension of Polyvinyl Alcohol," *Radiology*, 170(2):395-399 (Feb. 1989).

Rhine et al., "Polymers for Sustained Macromolecule Release: Procedures to Fabricate Reproducible Delivery Systems and Control Release Kinetics," *Journal of Pharmaceutical Sciences*, 69(3):265-270 (Mar. 1980).

Rump, A. et al., "Pharmacokinetics of Intraarterial Mitomycin C in the Chemoembolisation Treatment of Liver Metastases," *Gen. Pharmac.*, 27(4):669-671 (1996).

Schetky, "Shape-Memory Alloys," *Encyclopedia of Chemical Technology*, Third Edition, vol. 20, John Wiley & Sons, New York, pp. 726-736 (1982).

Schlief, R. et al., "Enhanced Color Doppler Echocardiography of the Left Heart After Intravenous Injection of a New Saccharide Based Agent in Humans", *Circulation*, vol. 82, No. 2, p. 28, Oct. 1990 (Abstract).

Schlief, R. et al., "Successful Opacification of the Left Heart Chamber on Echocardiographic Examination after Intravenous Injection of a New Saccharide Based Contrast Agent", *Echocardiography*, vol. 7, No. 1, pp. 61-64, Jan. 1990.

Schwarz et al., "The acoustic filter: An ultrasonic blood filter for the heart-lung machine," *J. Thorac. Cardiovasc. Surg.*, 104(6):1647-1653 (Dec. 1992).

Shafik, "Intraesophageal Polytef injection for the treatment of reflux esophagitis," *Surg. Endosc.*, 10:329-331 (1996).

Shape Shifters, http://www.sciam.com/tehbiz/0501scicit6.html, 3 pages, 2001.

Shung, K.K. et al., "Scattering of Ultrasound by Blood", *IEEE Transactions on Biomedical Engineering*, vol. BME-23, No. 6, pp. 460-467, Nov. 1976.

Sigelmann, R.A. et al., "Analysis and Measurement of Ultrasound Backscattering from an Ensemble of Scatters Excited by Sine-Wave Bursts", *Journal of Acoustical Society of America*, vol. 53, No. 4, pp. 1351-1355, Apr. 1973.

Sir-Spheres, Radioactive Implant (Yttrium-90 Microspheres), Sirex Medical, Inc., San Diego, CA, Nov. 6, 2000, pp. 1-15.

Sirtex Medical Limited—Product Description http://www.sirtex.com/?p=72, 3 pages (Retrieved from the internet on May 27, 2003).

Sirtex Medical Limited—Targeted Radiotherapy with SIR-Spheres http://www.sirtex.com/?p=57, 2 pages (Retrieved from the internet on May 27, 2003).

Siskin et al., "Pathologic Evaluation of a Spherical Polyvinyl Alcohol Embolic Agent in a Porcine Renal Model," *J Vasc. Interv. Radiol.*, 14:89-98 (2003).

Skotland, T. et al., "In Vitro Stability Analyses as a Model for Metabolism of Ferromagnetic Particles (Clariscan™), a Contrast Agent for Magnetic Resonance Imaging", *J. Pharm. Biomed. Anal.*, vol. 28, No. 2, pp. 323-329, Apr. 15, 2002.

"Smart Sutures Tie Themselves", Apr. 26, 2002, http://www.sciam.com/article.cfm?articleID=00047706-121F-1CD0-B4A8809EC588, 2 pages.

Smith et al., "Evaluation of Polydimethylsiloxane as an alternative in the Endoscopic Treatment of Vesicoureteral Reflux," *The Journal of Urology*, 152:1221-1224 (Oct. 1994).

Smith et al., "Left Heart Opacification with Peripheral Venous Injection of a New Saccharide Echo Contrast Agent in Dogs", *JACC*, vol. 13, No. 7, pp. 1622-1628, Jun. 1989.

Soppimath et al., "Controlled release of antihypertensive drug from the interpenetrating network poly(vinyl alcohol)-guar gum hydrogel microspheres," *J. Biomater. Sci. Polymer Edn*, 11(1):27-43 (2000).

Spickler, et al., "The MR appearance of endovascular embolic agents in vitro with clinical correlation", *Comput Med Imaging Graph*, vol. 14, No. 6, pp. 415-423, 1990.

Spies JB, "Georgetown University Medical Center. Uterine Fibroid Embolization (UFE). An alternative to surgery for patients with uterine fibroids. Literature Review," http://www.fibroidoptions.com/pr-lit.htm, 6 pages, Sep. 1, 2001.

Stancato-Pasik, A. et al., "Obstetric Embolotherapy: Effect on Menses and Pregnancy", *Radiology*, vol. 204, No. 3, pp. 791-793, Sep. 1997.

Stein, R. et al., "Targeting Human Cancer Xenografts with Monoclonal Antibodies Labeled Using Radioiodinated, Diethylenetriaminepentaacetic Acid-appended Peptides", *Clinical Cancer Research*, vol. 5, No. 10, pp. 3079-3087, Oct. 1999 (Supplement).

Strasnick et al., "Transcutaneous Teflon® Injection for Unilateral Vocal Cord Paralysis: An Update," *The Laryngoscope*, 101:785-787 (Jul. 1991).

Stridbeck, H. et al, "Collateral Circulation Following Repeated Distal Embolization of the Hepatic Artery in Pigs," *Invest. Radiol.*, 19(3):179-183 (1984).

Strunk, et al., "Treatment of congenital coronary arteriovenous malformations with microparticle embolization", *Cathet Cardiovasc Diagn*, vol. 22, No. 2, pp. 133-136, 1991.

Swanson DA et al., "The role of embolization and nephrectomy in the treatment of metastatic renal carcinoma", *Urologic Clinics of North America*, 7(3):719-730, 1980. University of Pennsylvania Cancer Center—Oncolink, http://www.oncolink.upenn.edu/pdg_html/cites/00/00585.html.

Tabata et al., "Tumor accumulation of poly(vinyl alcohol) of different sizes after intravenous injection", *Journal of Controlled Release*, vol. 50, pp. 123-133, Jan. 2, 1998.

Tadavarthy et al., "Polyvinyl Alcohol (Ivalon)—A New Embolic Material", *The American Journal of Roentgenology Radium Therapy and Nuclear Medicine*, vol. 125, No. 3, pp. 609-616, Nov. 1975.

Tadavarthy et al., "Polyvinyl Alcohol (Ivalon) as an Embolizing Agent", *Seminars in Interventional Radiology*, vol. 1, No. 2, pp. 101-109, Jun. 1984.

Tamatani, S. et al., "Histological Interaction of Cultured Endothelial Cells and Endovascular Embolic Materials Coated with Extracellular Matrix", *J. Neurosurg.*, vol. 86, No. 1, pp. 109-112, Jan. 1997.

Tao, et al., "Study of microspheres for embolization of hepatic artery", *Acta Pharrnaceutica Sinica*, vol. 23, No. 1, pp. 55-60, 1988.

Tao, et al., "Study of microspheres for embolization of hepatic artery", (Translation) *Acta Pharmaceutica Sinica*, vol. 23, No. 1, pp. 55-60, 1988.

Terada, et al., "Preoperative embolization of meningiomas fed by ophthalmic branch arteries", *Surg Neurol*, vol. 45, No. 2, pp. 161-166, 1996.

Thanoo, et al., "Controlled release of oral drugs from cross-linked polyvinyl alcohol microspheres", *J Pharm Pharmacol*, vol. 45, No. 1, pp. 16-20, 1993.

Thanoo, B. C. et al., "Preparation and Properties of Barium Sulphate and Methyl Iothalamate Loaded Poly(vinyl Alcohol) Microspheres as Radiopaque Particulate Emboli," *Journal of Applied Biomaterials*, 2:67-72 (1991).

Thanoo, et al., "Tantalum loaded silicone micropsheres as particulate emboli", *J Microencapsul*, vol. 8, No. 1, pp. 95-101, 1991.

Thelen, V.M. et al., "Catheter Embolisation of Metastasising Renal Carcinomas Using Butyle-2-cyano-acrylate", *Fortschr. Rontgenstr.*, vol. 124, No. 3, pp. 232-235, Mar. 1976 (English Abstract included).

The Vanderbilt-Ingram Cancer Center, "Kidney Cancer," http://www.mc.Vanderbilt.Edu/cancer/cancerinfo/kidney.html, 1 page, 2001.

Tian et al., "Design and synthesis of amphiphilic poly (ethylene glycol) derivatives as micellar drug delivery systems," *Polymer Preprints*, 43(2):719-720 (Fall 2002).

Tikkakoski, et al., "Preoperative embolization in the management of neck paragangliomas", *Laryngoscope*, vol. 107, pp. 821-826, 1997.

Toon, "Improving a Key Weapon Against Cancer," Research Horizons, pp. 11-12, Spring/Summer 2001.

Touho, et al., "Intravascular treatment of spinal arteriovenous malformations using a microcatheter—with special reference to serial xylocaine tests and intravascular pressure monitoring", *Surgical Neurology*, vol. 42, No. 2, pp. 148-156, 1994.

University Medical Center SUNY Stony Brook, Department of Urology, "Variococele and its treatment," http://www.hsc.sunysb.edu/urology/male_inf...variocoele_and_its_treatment.html, 8 pages, Last Updated on Mar. 12, 2001.

Vivas S et al., "Arterioportal fistula and hemobilia in a patient with hepatic transplant", Gastroenterol Hepatol, 21(2):88-9, http://www.doyma.es/copiani/revistas/gastro/abstr/abs_p080.html, Feb. 1998 (English Abstract included).

Vogel F, "Nonsurgical Management of Uterine Fibroids," http://www.holyname.org/brochure/fibroids.html, 5 pages.

Wakhloo, et al., "Extended preoperative polyvinyl alcohol microembolization of intracranial meningiomas: Assessment of two embolization techniques", *American Journal of Neuroradiology*, vol. 14, pp. 571-582, 1993.

Walker WJ, "Non Surgical Treatment of Fibroids in the UK by Uterine Artery Embolisation—An Alternative to Hysterectomy, Myomectomy and Myolysis," http://www.fibroids.co.uk/thepaper.html, 2 pages, 2002.

Walsh RM et al., "Role of Angiography and Embolization for Acute Massive Upper Gastronintestinal Hemorrhage," *J. Gastrointest. Surg.*, 3:61-66 (1999).

Waltman, A.C. et al., "Technique for Left Gastric Artery Catheterization", *Radiology*, vol. 109, No. 3, pp. 732-734, Dec. 1973.

White, Jr., "Embolotherapy in Vascular Disease," *American Journal of Roentgenology*, 142:27-30 (Jan. 1984).

Widder, K.J. et al., "Selective Targeting of Magnetic Microspheres Containing Adriamycin: Total Remission in Yoshida Sarcoma-Bearing Rats", *Proceedings of the 16th Annual Meeting of American Society of Clinical Oncology*, May 26-27, 1980, San Diego, CA, p. 261.

Widder, K. et al., "Magnetic Microspheres: Synthesis of a Novel Parenteral Drug Carrier", *Journal of Pharmaceutical Sciences*, vol. 68, No. 1, pp. 79-82, Jan. 1979.

Wikholm G et al., "Embolization of Cerebral Arteriovenous Malformations: Part I—Technique, Morphology, and Complications", Neurosurgery, 39(3):448-459 (Sep. 1996).

Winters et al., "Periurethral injection of collagen in the treatment of intrinsic sphincteric deficiency in the female patient," *The Urologic Clinics of North America*, 22(3):673-678 (Aug. 1995).

Worthington-Kirsch RL, "Interventionalists offer management option for uterine fibroids," *Diagnostic Imaging*, 21(3):47-49, Mar. 1999, http://www.dimag.com/references/9903wortrefs.html.

Worthington-Kirsch, et al., "Uterine arterial embolization for the management of leiomyomas: Quality-of-life assessment and clinical response", *Radiology*, vol. 208, No. 3, 625-629, 1998.

Wright, K.C. et al., "Partial Splenic Embolization Using Polyvinyl Alcohol Foam, Dextran, Polystyrene, or Silicone," *Radiology*, 142:351-354, Feb. 1982.

Wu, A.M., "Engineered Antibodies for Breast Cancer Imaging and Therapy," http://www.cbcrp.org/research/PageGrant.asp?grant_id=111, 3 pages, 1996.

Yamada, T. et al., "Extended Intraarterial Cisplatin Infusion for Treatment of Gynecologic Cancer After Altercation of Intrapelvic Blood Flow and Implantation of a Vascular Access Device", *Cardiovasc. Intervent. Radial.*, vol. 19, pp. 139-145, 1996.

Yamashita, Y. et al., "Transcatheter Arterial Embolization of Obstetric and Gynaecological Bleeding: Efficacy and Clinical Outcome", *British Journal of Radiology*, vol. 67, pp. 530-534, Jun. 1994.

Yoon et al., "Surface Immobilization of Galactose onto Aliphatic Biodegradable Polymers for Hepatocyte Culture," *Biotechnol. Bioeng.*, 78(1):1-10 (Apr. 5, 2002).

Yusi et al., "Submuscosal Injection of Polyvinyl Alcohol in Artificially Created Vesico-Ureteral Reflux: a Preliminary Report," *Asian J. Surg.*, 18(2):122-127 (Apr. 1995).

Zisch et al., "Covalently conjugated VEGF-fibrin matrices for endothelialization," *Journal of Controlled Release*, 72:101-113 (2001).

Ziskin, M.C. et al., "Contrast Agents for Diagnostic Ultrasound", *Investigative Radiology*, vol. 7, No. 6, pp. 500-505, Nov.-Dec. 1972.

Zou, Ying-hua, et al. "Experimental Canine Hapatic Artery Embolization with Polyvinyl Alcohol Microspheres," *Zhong Hua Fang-She Xue ZaZhi*, 23(6):330-332 (1989).

Zou, Ying-hua, et al. "Experimental Canine Hapatic Artery Embolization with Polyvinyl Alcohol Microspheres," Translation, *Zhong Hua Fang-She Xue ZaZhi*, 23(6):330-332 (1989).

\* cited by examiner

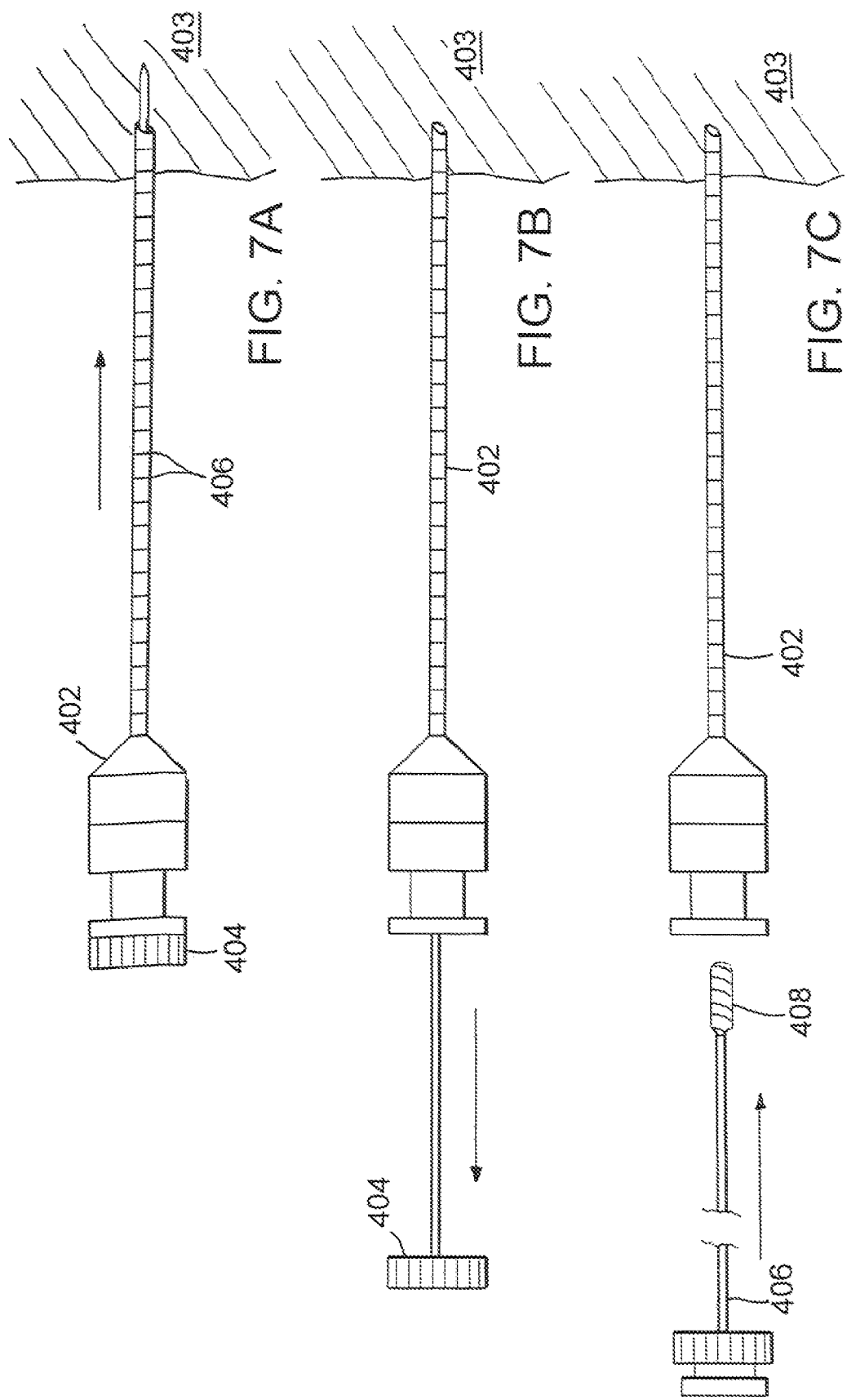

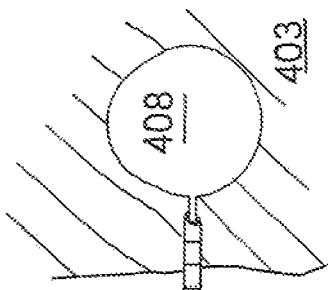
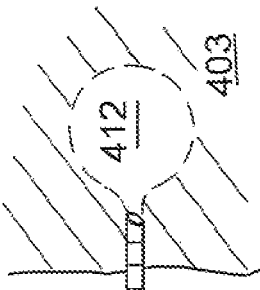
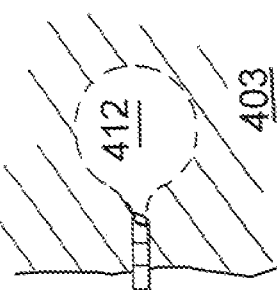
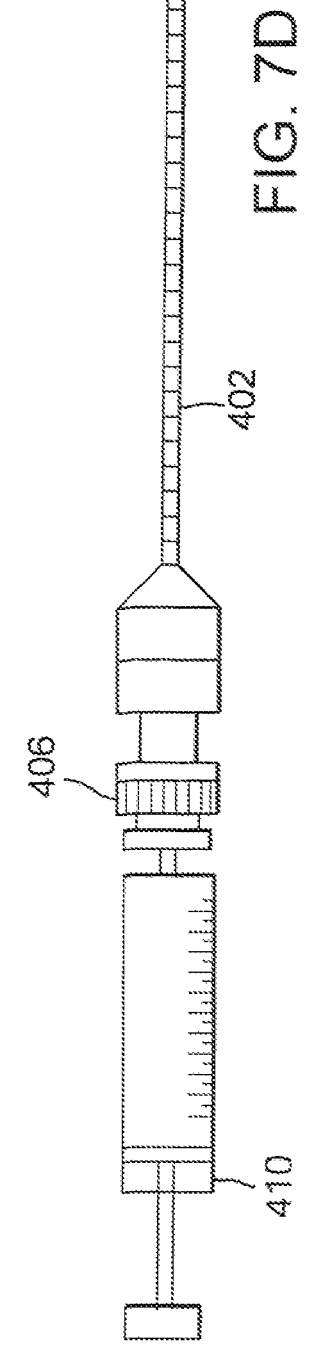
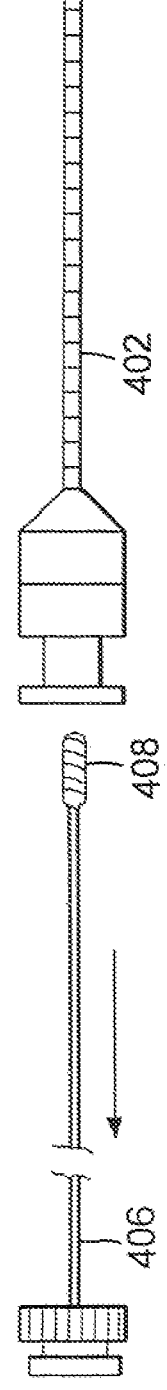
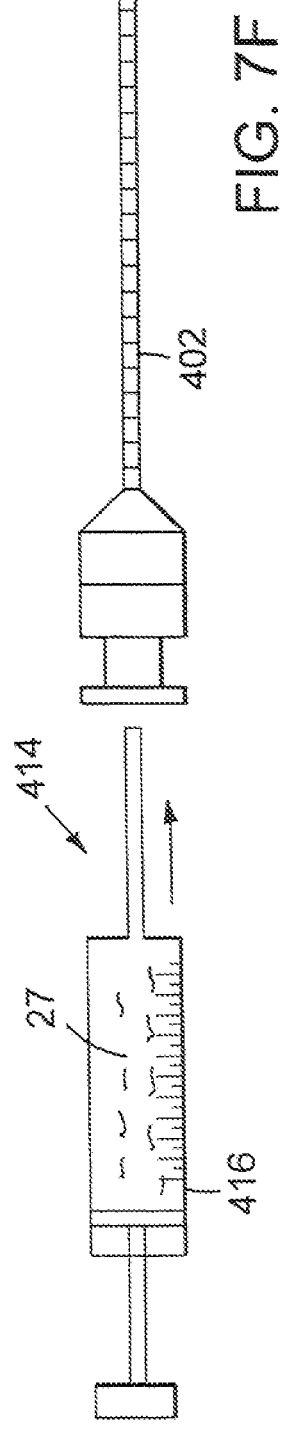
FIG. 7D
FIG. 7E
FIG. 7F

TISSUE TREATMENT

CLAIM OF PRIORITY

This application is a continuation of and claims priority to U.S. patent application Ser. No. 10/231,664, now U.S. Pat. No. 7,131,997, entitled "Tissue Treatment" and filed on Aug. 30, 2002 which is a continuation-in-part of and claims priority to U.S. patent application Ser. No. 10/215,594, entitled "Embolization" and filed on Aug. 9, 2002, which is a continuation-in-part of U.S. patent application Ser. No. 10/109,966, now U.S. Pat. No. 7,094,369, entitled "Processes for Manufacturing Polymeric Microspheres" and filed on Mar. 29, 2002. U.S. Ser. No. 10/231,664, now U.S. Pat. No. 7,131,997 also claims priority to U.S. Patent Application Ser. No. 60/388,446, now abandoned, entitled "Bulking Agents" and filed on Jun. 12, 2002. The entire contents of these applications are hereby incorporated by reference.

TECHNICAL FIELD

This invention relates to the treatment of tissue, such as the introduction of particles into body tissue for repair and/or augmentation.

BACKGROUND

The body includes various passageways through which bodily matter or fluids, such as urine, can flow. The flow of material through the passageways is in part affected by tissue surrounding the passageways. For example, the tissue can constrict and cause a passageway to narrow or to close, thereby restricting flow of material through the passageway.

In some disorders, the tissue can no longer affect a passageway. For example, while urine normally flows down in one direction from the kidneys, through tubes called ureters, and to the bladder, in vesicoureteral reflux (VUR), urine can flow abnormally from the bladder back into the ureters. In gastroesophageal reflux disease (GERD), sometimes called "reflux", acid from the stomach can flow back into the swallowing tube, or esophagus. Other disorders include, for example, urinary incontinence, i.e., loss of urinary control, and fecal incontinence.

One method of treating such disorders includes placing, e.g., injecting, a building material in the tissue adjacent to the passageway. The bulking material can narrow the passageway and, by providing bulk, allows the tissue to constrict the passageway more easily.

SUMMARY

This invention relates to the treatment of tissue.

In one aspect, the invention features a method of treating tissue including placing substantially spherical polymer particles in the tissue. The particles have an interior region having relatively large pores and a first region substantially surrounding the interior region having fewer relatively large pores than the interior region.

Embodiments may include one or more of the following features. The particles are injected into the tissue. The particles are injected percutaneously. The particles are delivered through a catheter. The method includes forming a cavity in the tissue, and placing the particles in the cavity. The tissue is adjacent to a body passageway. The passageway is defined by a ureter. The tissue is adjacent to a body passageway, and the particles are placed in an amount effective to narrow the passageway.

The particles can be polyvinyl alcohol. The polyvinyl alcohol can be 1,3 diol acetalized. The particles can include a polysaccharide. The polysaccharide can include alginate.

The particles can include a therapeutic agent.

In another aspect, the invention features a method of treating an individual. The method includes placing a therapeutically effective amount of substantially spherical particles including polyvinyl alcohol in a tissue of the individual. The particles have an interior region having relatively large pores and a first region substantially surrounding the interior region having fewer relatively large pores than the interior region.

Embodiments can include one or more of the following features.

The method further includes selecting the individual diagnosed with gastroesophageal reflux disease. The tissue is adjacent to a gastrointestinal tract. The method further includes selecting the individual diagnosed with vesicoureteral reflux. The tissue is adjacent to a ureter.

The method can further include selecting an individual diagnosed with urinary incontinence, fecal incontinence, intrinsic sphincteric deficiency, and/or vocal cord paralysis. The method can further include selecting an individual in need of a reconstructive or cosmetic procedure.

The particles can be placed percutaneously and/or through a catheter.

In another aspect, the invention features a method of delivering a therapeutically effective amount of substantially spherical polymer particles. The particles include polyvinyl alcohol and include an interior region having relatively large pores and a surface region having fewer relatively large pores. The particles can have a diameter of about 1200 micron or less, a surface with a predominant pore size of about 2 micron or less and pores interior to surface of about 10 micron or more, and/or a surface region from about 0.8 r to r, the predominant pore size in the surface region being smaller than the predominant pore size in a region C to 0.3 r.

Embodiments may also include one or more of the following. The relatively large pores are about 20 or 30 micron or more. The surface region is about r to 0.8 r. The surface region is about r to 2/3 r. The particles include a body region from about 2/3 r to r/3 including intermediate size pores and the body region has more intermediate size pores than the surface region. The center region is from about r/3 to C, the outer region including large size pores and the body region has fewer large size pores than the center region. The intermediate size pores are about 2 to 18 microns. The surface region is substantially free of pores greater than about 5 micron.

Embodiments may also include one of the following. The predominant pore size progressively increases from surface to the center of the particle. The predominant pore size on the particle surface is about 1 micron or less. The particles have a surface region from about (2 r)/3 to the surface wherein the predominant pore size is in the range of about 1 micron or less. The predominant pore size is about 0.1 micron or less. Interior of said surface region, the particles have a predominant pore size in the range of about 2 to 35 microns. The particles include a center region from about r to r/3 in which the predominant pore size is about 20 to 35 micron. The particles have a body region from r/3 to (2 r)/3 in which the predominant pore size is about 2 to 18 micron. The particles have a surface region from about (2 r)/3 to the periphery and the predominant pore size in the surface region is about 10% or less than the predominant pore size in the interior to the surface region. The particles include a surface region from about 0.8 r to r wherein the predominant pore size is about 1 micron or less. The particles include a region from about C to 0.8 r includes pores having a diameter of 10 microns or more.

The region C to 0.8 r has a predominant pore size of about 3.5 to 2 micron. The particles have a density of about 1.1 to about 1.4 g/cm$^3$. The particles have a density of about 1.2 to 1.3 g/cm$^3$. The particles have a sphericity of about 90% or more. The particles have an initial sphericity of about 97% or more. The particles have a sphericity of about 0.90 after compression to about 50%. The particles have a size uniformity of about +15% or more.

Embodiments may also include one or more of the following. The particles include about 1% or less polysaccharide. The polysaccharide is alginate. The alginate has a galuronic acid content of about 60% or greater. The particles are substantially insoluble in DMSO. The particles are substantially free of animal-derived compounds. The polyvinyl alcohol is composed of substantially unmodified polyvinyl alcohol prepolymer. The polyvinyl alcohol is predominantly intrachain 1,3-diols acetalized. The composition includes saline and/or contrast agent. The particles and/or composition are sterilized.

Embodiments may also include one or more of the following. The gelling compound is a polysaccharide. The gelling compound is alginate. The alginate has a galuronic acid content of about 60% or more. The drops are contacted with a gelling agent. The gelling agent is a divalent cation. The cation is Ca+2. The base polymer is PVA. The PVA is reacted by acetalization. The PVA has a molecular weight of about 75,000 g/mole or greater. The viscosity of the base polymer and gelling compound is modified prior to forming said drops. The viscosity is modified by heating. The drops are formed by vibratory nebulization.

Embodiments may also include one or more of the following. Administration is by percutaneous injection. Administration is by a catheter. The particles are introduced to the body through a lumen, and the lumen has a smaller diameter than the particles.

The particles can be tailored to a particular application by varying particle size, porosity gradient, compressibility, sphericity and density of the particles. The uniform size of the spherical particles can, for example, fit through the aperture of a needle or a catheter for administration by injection to a target site without partially or completely plugging the lumen of the needle or the catheter. Size uniformity of +15% of the spherical particles allows the particles to stack evenly.

Embodiments may have one or more of the following advantages. The particles are relatively inert and biocompatible (e.g., they do not trigger an allergic or cytotoxic response). The particles do not substantially migrate, which can cause adverse effects. The particles are relatively non-bioresorbable. As a result, the particles retain their efficacy, and the need for repeated procedures is reduced, which can lower cost, trauma, and/or complications. The particles can be used in a variety of applications.

Other aspects, features, and advantages of the invention will be apparent from the description of the preferred embodiments thereof and from the claims.

DESCRIPTION OF DRAWINGS

FIGS. 7A-7F illustrate a method of treating tissue.

DETAILED DESCRIPTION

Figure 1A:
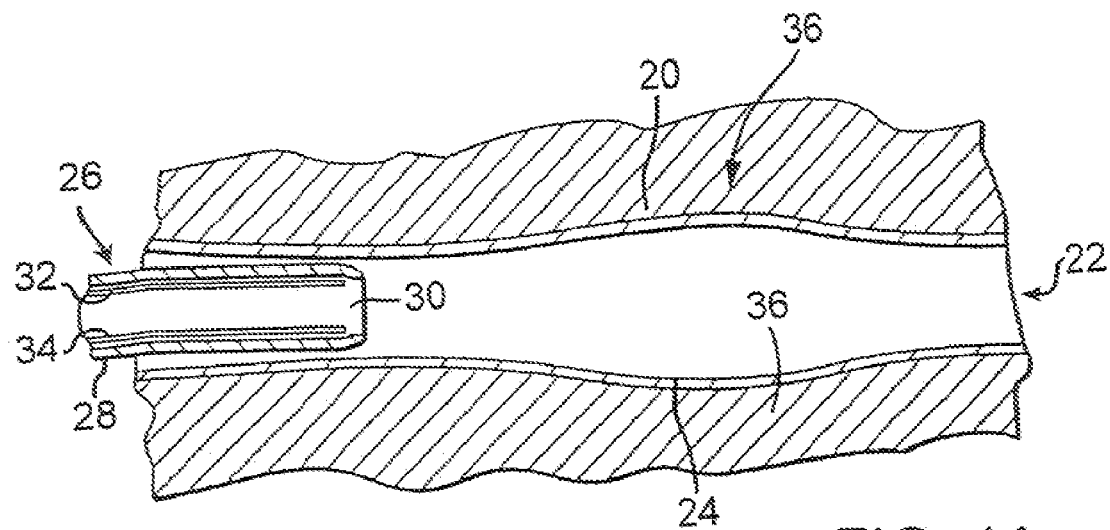
FIGS. 1A and 1B illustrate a method of treating tissue.
Figure 1B:
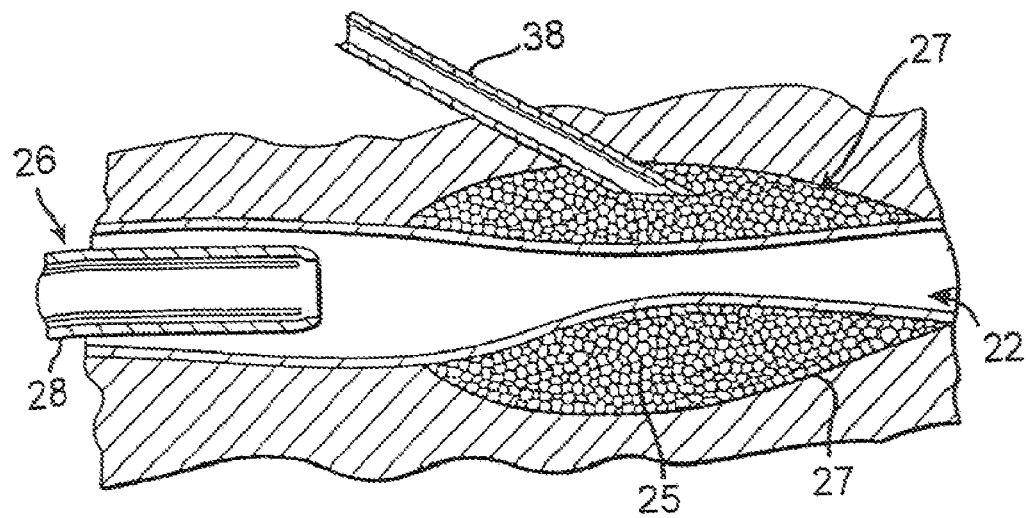

Referring to FIGS. 1A and 1B, a method of treating tissue 20, here, located adjacent to a passageway 22, is shown. Passageway 22 is defined by a wall 24, e.g., of a urethra or a ureter. The method generally includes placing a composition 27 including highly water insoluble, high molecular weight polymer particles 25 into tissue 20. Particles 25, e.g., acetalized polyvinyl alcohol, have a substantially uniform shape and a symmetric compressibility. Particles 25 can increase bulk and localize compression, thereby reducing the size of passageway 22 and assisting tissue 20 in closing to reduce (e.g., minimize or eliminate) flow of matter, such as urine, through the passageway. As described below, composition 27 can include other materials, such as a carrier, a contrasting agent, and/or a therapeutic agent.

As shown, the method includes injecting composition 27 into tissue 20. Before composition 27 is injected, a cytoscope 26 is introduced into passageway 22 by conventional cytoscopic techniques. Cytoscope 26 includes an elongated sheath 28 that defines a channel 30. In channel 30, cytoscope 26 includes a light emitting element 32 (such as an optic fiber) and a viewing element 34. Cytoscope 26 is positioned at a location selected to view a target area 36 to be treated.

Figure 2:
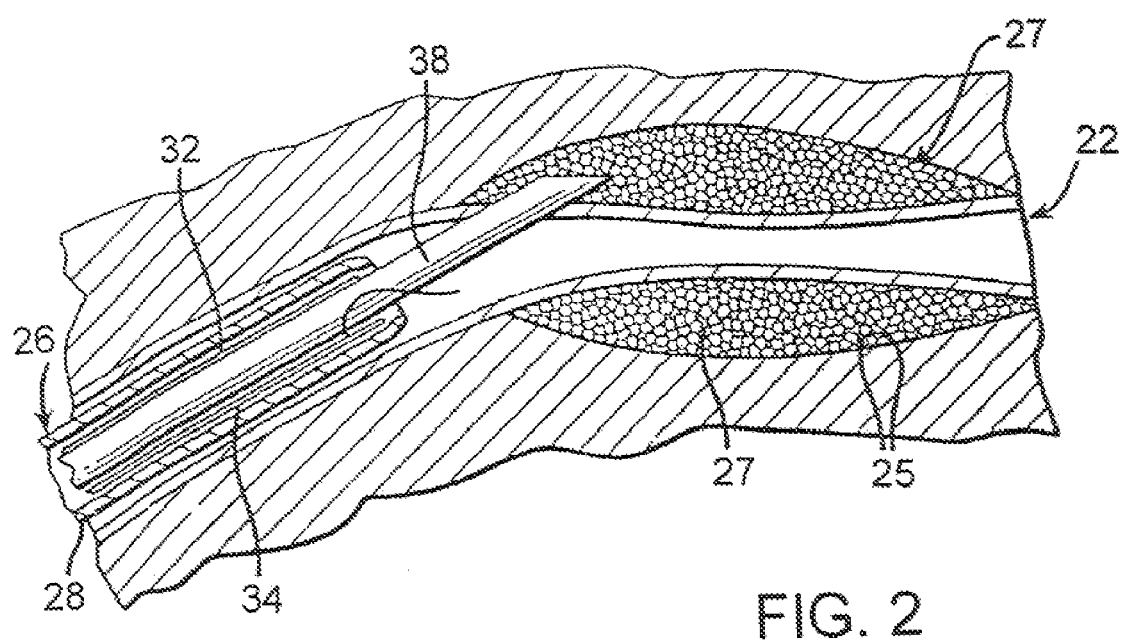
FIG. 2 illustrates a method of treating tissue.

Subsequently, a needle 38 is inserted into tissue 20 to target area 36, but without penetrating wall 24. Composition 27 including particles 25 is then injected from a syringe (not shown) to area 36. The progress of the injection can be monitored, for example, by viewing changes, e.g., narrowing, in passageway 22 through cytoscope 26 or by fluoroscopic or spectroscopic techniques, e.g., in embodiments in which composition 27 includes a contrasting agent (described below). In other embodiments, referring to FIG. 2, needle 38 is inserted through channel 30 of cytoscope 26 to deliver composition 27.

The methods described above can be used for a variety of medical applications, such as for the treatment of intrinsic sphincteric deficiency (ISD). For example, composition 27 can be used to treat urinary incontinence. Composition 27 can be injected into the tissue of the urinary tract, wherein the selected site can be, for example, the mucosal tissue of the bladder neck, the urethra or urethral sphincter. The resulting bulking or augmentation of the urethral tissue can reduce or restrict the size of the urethra or urinary passage and thus assist in overcoming incontinence. Methods and techniques of placing bulking materials for the treatment of urinary incontinence are described in Namiki, "Application of Teflon Paste for Urinary Incontinence—Report of Two Cases", *Urol. Int.*, Vol. 39, pp. 280-282 (1984); Politano et al., "Periurethral Teflon Injection for Urinary Incontinence", *The Journal of Urology*, Vol. 111, pp. 180-183 (1974); Winters, et al., "Periurethral Injection of Collagen in the Treatment of Intrinsic Sphincteric Deficiency in the Female Patient", *Urologic Clinics of North America*, 22(3):473-478 (1995); U.S. Pat. No. 5,007,940; U.S. Pat. No. 5,158,573; U.S. Pat. No. 5,116,387; and references cited therein.

Composition 27 can be injected into the tissue of the anal canal, wherein the selected site can be, for example, the mucosal tissue of the anal canal, such as near the internal or external anal sphincter muscle. The resulting bulking or augmentation of the tissue can restrict the size of the sphincter or anal passage and thus assist in reducing fecal or anal incontinence. Composition 27 can also be used to treat, e.g., repair, structurally defective and/or inadequately functioning muscles of the anal sphincter. For example, a physician can perianally inject composition 27 into a deformity, e.g., a keyhole deformity resulting from trauma or surgery, using one or more injections, until the deformity is repaired or the treated area is restored to its proper form. Methods of placing biocompatible materials to treat the sphincter muscles are described in Freed, U.S. Pat. No. 5,490,984.

Composition 27 can be used to treat vesicoureteral reflux. For example, composition 27 can be placed in the subureteral tissue to compress the ureter, thereby reducing the reflux of urine into the ureter. Methods for delivering a composition to treat vesicoureteral reflux are described in Capozza, et al., "Endoscopic Treatment of Vesico-Ureteric Reflux and Urinary Incontinence: Technical Problems in the Pediatric Patient," *Br. J. Urol.*, 75: 538-542 (1995); and Smith et al., "Evaluation of Polydimethylsiloxane as an Alternative in the Endoscopic Treatment of Vesicoureteral Reflux", *J. Urol.*, 152: 1221-1224, 1994.

Composition 27 can be applied to gastroesophageal reflux disease (GERD) applications. Composition 27 can be injected into the mucosal tissue of the upper gastrointestinal tract, wherein the selected site may be, for example, the mucosal tissue of the cardiac orifice of the stomach, which opens into the esophagus. The resulting bulking or augmentation of the tissue can restrict the size of the passage and thus assist in reducing gastric fluids refluxing into the esophagus. Methods and techniques are described, for example, in Shafik, "Intraesophageal Polytef Injection for the Treatment of Reflux Esophagitis", *Surg. Endoscopy*, 10:329-331 (1996), and references cited therein.

Composition 27 can also be used to treat other conditions, such as vocal cord paralysis, e.g., to restore glottic competence in cases of paralytic dysphonia. Such general treatment methods are described in Hirano et al., "Transcutaneous Intrafold Injection for Unilateral Vocal Cord Paralysis: Functional Results", *Ann. Otol. Rhinol Laryngol.*, Vol. 99, pp. 598-604 (1990); Strasnick et al., "Transcutaneous Teflon® Injection for Unilateral Vocal Cord Paralysis: An Update", *Laryngoscope*, Vol. 101, pp. 785-787 (July 1991); and references cited therein.

In other embodiments, composition 27 is used to treat soft tissue. For example, composition 27 can be used for reconstructive or cosmetic applications, e.g., surgery. Examples of applications include reconstruction of cleft lips; scars, e.g., depressed scars from chicken pox or acne scars; indentations resulting from liposuction; wrinkles, e.g., glabella frown wrinkles; and soft tissue augmentation of tin lips. Composition 27 can be used as a graft material or a filler to fill and/or to smooth out soft tissue defects. For example, composition 27 can be injected percutaneously under a defect until the appearance of the defect, e.g., a wrinkle, is reduced. Procedures and techniques are describe, for example, in Ersek et al., "Bioplastique: A New Textured Copolymer Microparticles Promises Permanence in Soft-Tissue Augmentation", *Plastic and Reconstructive Surgery*, Vol. 87, No. 4, pp 693-702 (April 1991); Lemperle et al., "PMMA Microspheres for Intradermal Implantation: Part I. Animal Research", *Annals of Plastic Surgery*, Vol. 26, No. 1, pp. 57-63 (1991); and references cited therein.

For the applications described above, the amount of composition 27 delivered can vary based on the nature, location and severity of the condition to be treated and the route of administration, the size of particles 25, and factors relating to the patient. A physician treating the condition, disease or disorder can determine an effective amount of composition 27. An effective amount of composition 27 refers to the amount sufficient to result in amelioration of symptoms or a prolongation of survival of the patient.

In other embodiments, particles 25 can also be used for implantable prostheses, such as mammary or breast implants, penile implants, or testicular prostheses. For example, particles 25 can be encased in a shell made of compliant material, such as silicone elastomers, polyolefins, polyurethanes, ethylene-propylene diene monomers, or ethylene-propylene rubbers. In embodiments, particles 25 can be used without a shell because they can remain at the delivery site and do not migrate. Prostheses are described, for example, in U.S. Pat. No. 5,941,909; U.S. Pat. No. 6,060,639; U.S. Pat. No. 5,063,914; and references cited therein.

The Composition

As described above, composition 27 includes polymer particles 25. In embodiments, composition 27 also includes a carrier, a contrasting agent, and/or a therapeutic agent.

The particles: Particles 25 are substantially formed of polymer such as a highly water insoluble, high molecular weight polymer. As will be discussed below, a preferred polymer is high molecular weight polyvinyl alcohol (PVA) that has been acetalized. Preferably, the particles are substantially pure intachain 1,3 acetalized PVA and substantially free of animal derived residue such as collagen. In embodiments, the particles include a minor amount, e.g. less than about 0.2 weight %, of alginate or another polysaccharide or gelling material.

Figure 3A:
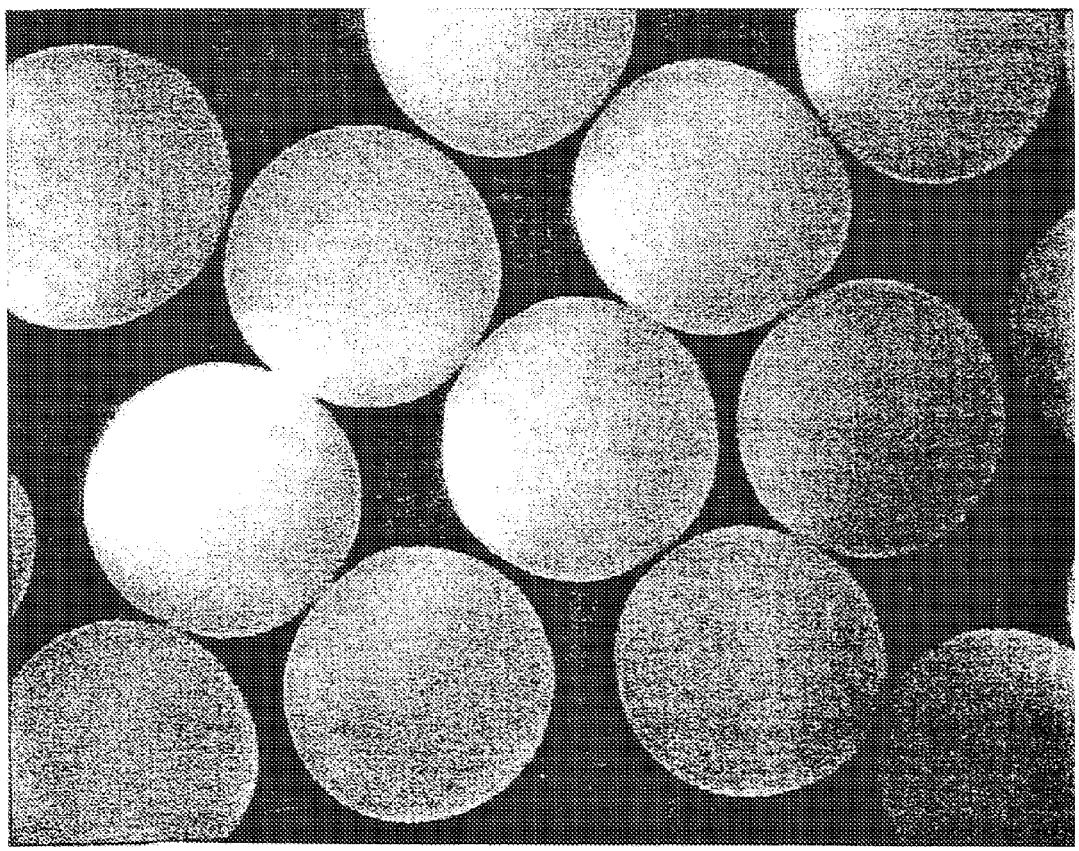
FIG. 3A is a light micrograph of a collection of hydrated particles.
Figure 3B:
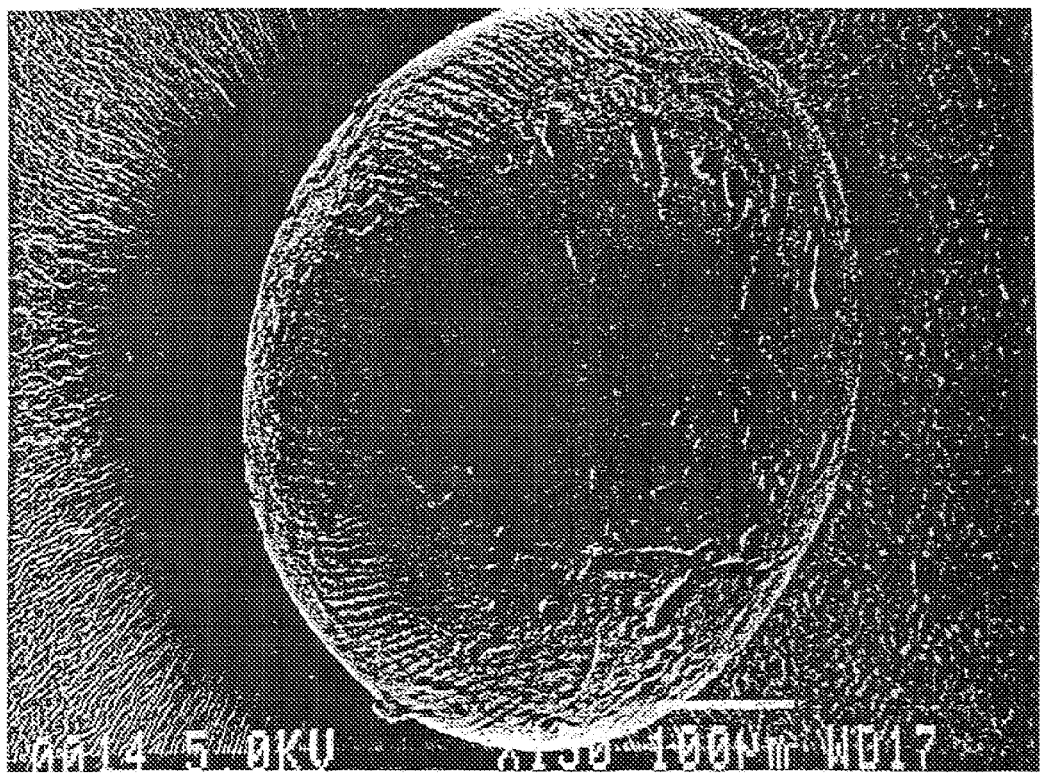
FIG. 3B is a scanning electron microscope (SEM) photograph of the particle surface.
Figure 3C:
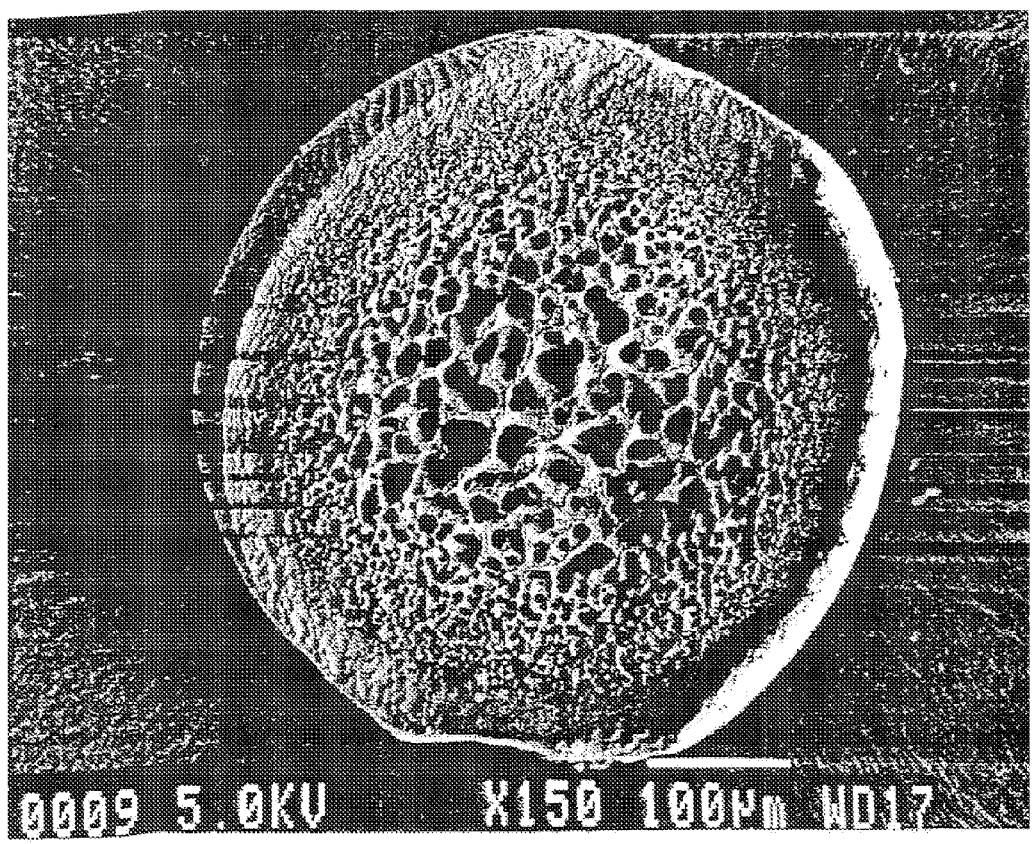
FIGS. 3C-3E are cross-sections of the particles.
Figure 3C:
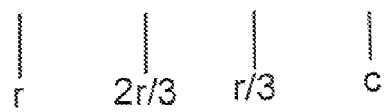
Figure 3D:
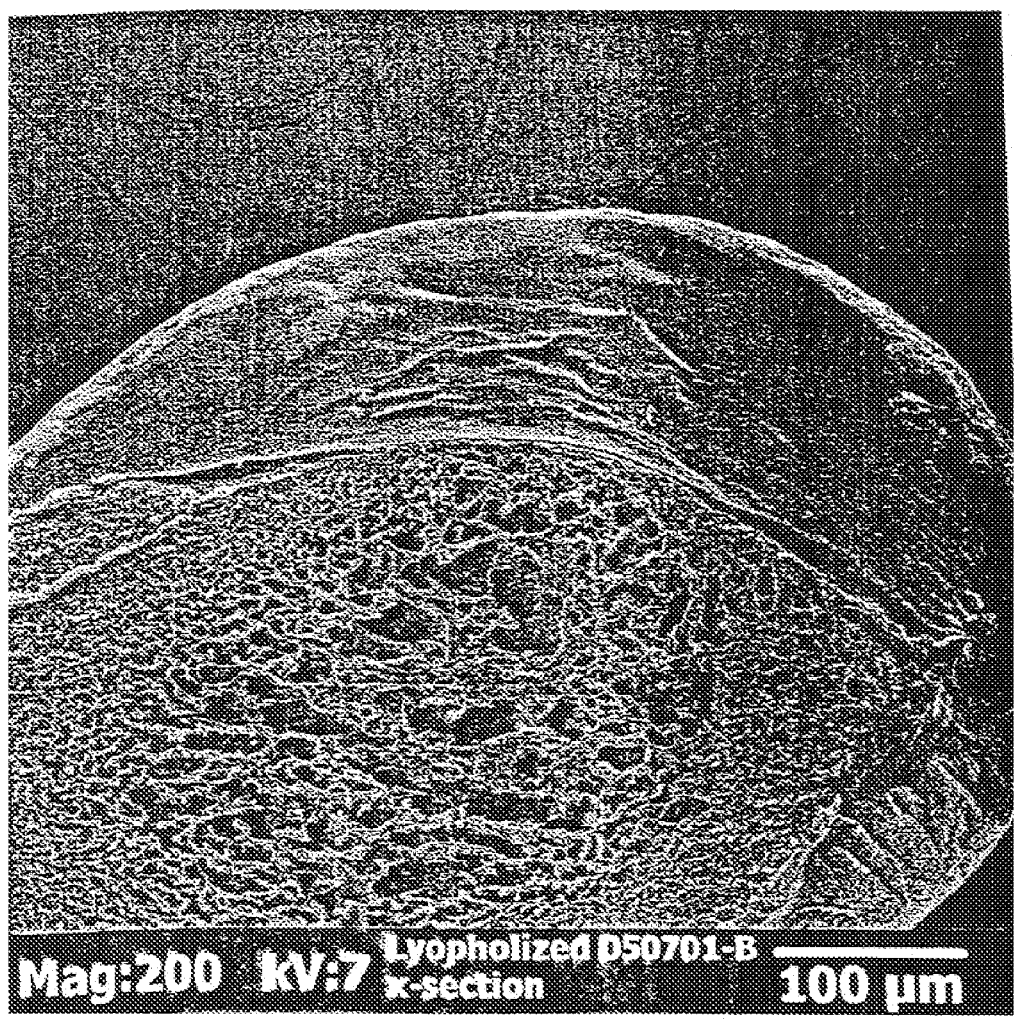
Figure 3E:
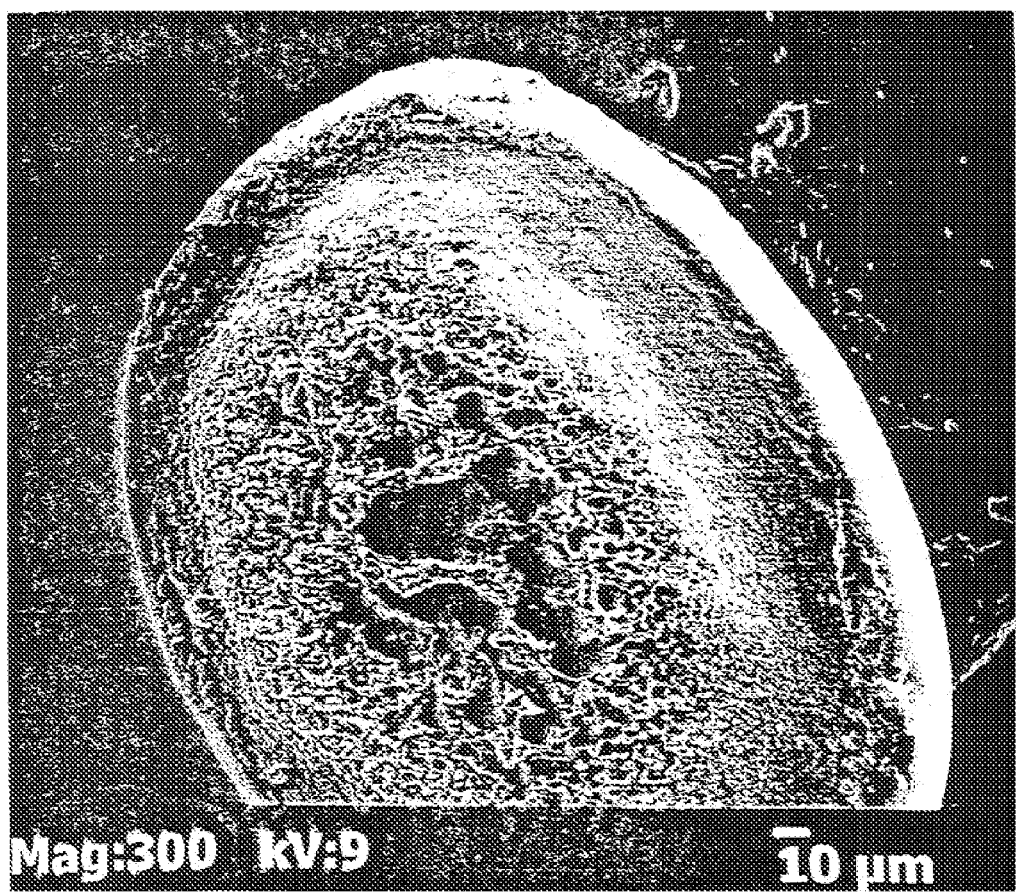

Referring to FIG. 3A, particles 111 have a substantially uniform spherical shape and size. Referring to FIG. 3B, each particle has a well-defined outer spherical surface including relatively small, randomly located pores. The surface appears substantially smooth, with some larger surface morphology such as crevice-like features. Referring to FIGS. 3C-3E, SEM images of cross-sections through particles, the body of the particle defines pores which provide compressibility and other properties. Pores near the center of the particle are relatively large and pores near the surface of the particle are relatively small.

The region of small pores near the periphery of the particle is relatively stiff and incompressible, which enhances resistance to shear forces and abrasion. In addition, the variable pore size profile produces a symmetric compressibility and, it is believed, a compressibility profile such that the particles are relatively easily compressed from a maximum, at rest diameter to a smaller, compressed first diameter but compression to even smaller diameter requires substantially greater force. A variable compressibility profile is believed to be due to the presence of a relative weak, collapsible inter-pore wall structure in the center region where the pores are large, and a stiffer inter-pore wall structure near the surface of the particle, where the pores are more numerous and relatively small. The variable pore size profile also is believed to enhance elastic recovery after compression. The pore structure also influences the density of the particles and the rate of carrier fluid or body fluid uptake.

The particles can be delivered through a needle having a lumen area that is smaller, e.g. 50% smaller or less, than the uncompressed cross-sectional area of the particles. As a result, the particles are compressed to pass through the needle for delivery into the body. The compression force is provided indirectly by increasing the pressure applied to the carrier fluid by depressing the syringe plunger. The particles are relatively easily compressed to diameters sufficient for delivery through the needle into the body. The robust, rigid surface region resists abrasion when the particles contact hard surfaces such as syringe surfaces, and the needle lumen wall (e.g.

stainless steel) during delivery. Once in the body, the particles substantially recover to original diameter and shape, and form a dense mass. The compression can be limited by the compression profile of the particles, and the number of particles needed at a particular target area can be reduced.

In embodiments, the particles have a diameter of about 1500 or 1200 microns or less, and about 10 microns or more, e.g. about 400 microns or more and the pores are about 50 or 35 to 0.01 micron. The particles can be classified in size ranges of about 500-700 microns, about 700-900 microns, or about 900-1200 microns. The particles typically have a mean diameter in approximately the middle of the range and variance of about 20% or less, e.g. 15% or 10% or less.

The particular size of the particles used can also be a function of their application. For example, for cosmetic applications, relatively small particles can be used to provide a more natural feel and to reduce a granular texture. Small particles can also be delivered through small needles, which can reduce psychological trauma and discomfort to the patient.

Referring particularly to FIG. 3C, the particles can be considered to include a center region, C, from the center of the particle to a radius of about r/3, a body region, B, from about r/3 to about 2 r/3 and a surface region, S, from 2 r/3 to r. The regions can be characterized by the relative size of the pores and the number of pores of given sizes. In embodiments, the center region has a greater number of relatively large pores than the body region and the surface region. The large pores are in the range of about 20 micron or more, e.g. 30 micron or more, or in the range of about 20 to 35 micron. The body region has a greater number of intermediate size pores than the surface region. The intermediate size pores are in the range of about 5 to 18 micron. In embodiments, the regions may also have different densities, with the density of the surface region being greater than the density of the body region, and the density of the body region being greater than the density of the center region.

The size of the pores in each of the regions can also be characterized by a distribution. In embodiments, the predominant pore size(s) in the center region being greater than the predominant pore size(s) in the body region and the predominant pore size(s) in the body region is greater than the predominant pore size(s) in the surface region. In embodiments, in the predominant pore size in the center region is 20 micron or more, e.g. 30 microns or more, or in the range of about 20 to 35 microns. The predominant pore size in the body region is about 18 micron or less, e.g. about 15 micron or less, or in the range of about 18 to 2 micron. The pores in the surface region are preferably predominantly less than about 1 micron, e.g. about 0.1 to 0.01 micron.

In embodiments, the predominant pore size in the body region is about 50 to 70% of the pore size in the center region and the pore size in the surface region is about 10% or less, e.g. about 2% of the pore size in the body region. The size of the pores on the outer surface of the particle is predominantly in the range of about 1 micron or less, e.g. about 0.1 or 0.01 micron. In embodiments, the surface and/or surface region is substantially free of pores having a diameter larger than about 10 micron or larger than about 1 micron. In embodiments, the predominant pore size is in the region 0.8 or 0.9 r to r is about 1 micron or less, e.g. 0.5 to 0.1 micron or less. The region from the center of the particle to 0.8 or 0.9 r has pores of about 10 micron or greater and/or has a predominant pore size of about 2 to 35 micron. In embodiments, the predominant pore size in the region 0.8 or 0.9 r to r is about 5% or less, e.g. 1% or 0.3% or less than the predominant pore size in the region from the center to 0.9 r. the largest pores in the particles can have a size in the range of 1% or 5% or 10% or more of the particle diameter, The size of the pores can be measured by viewing a cross-section as in FIG. 3C. For irregularly shaped pores, the maximum visible cross-section is used. The predominant pore size(s) can be found by measuring the size of the visible pores and plotting the number of pores as a function of size. The predominant pore size(s) are the sizes that are about the maximum in the distribution. In FIG. 3C, the SEM was taken on wet particles including absorbed saline, which were frozen in liquid nitrogen and sectioned. (FIG. 3B was taken prior to sectioning.) In FIGS. 3D and 3E, the particle was freeze-dried prior to sectioning and SEM analysis.

Figure 4A:
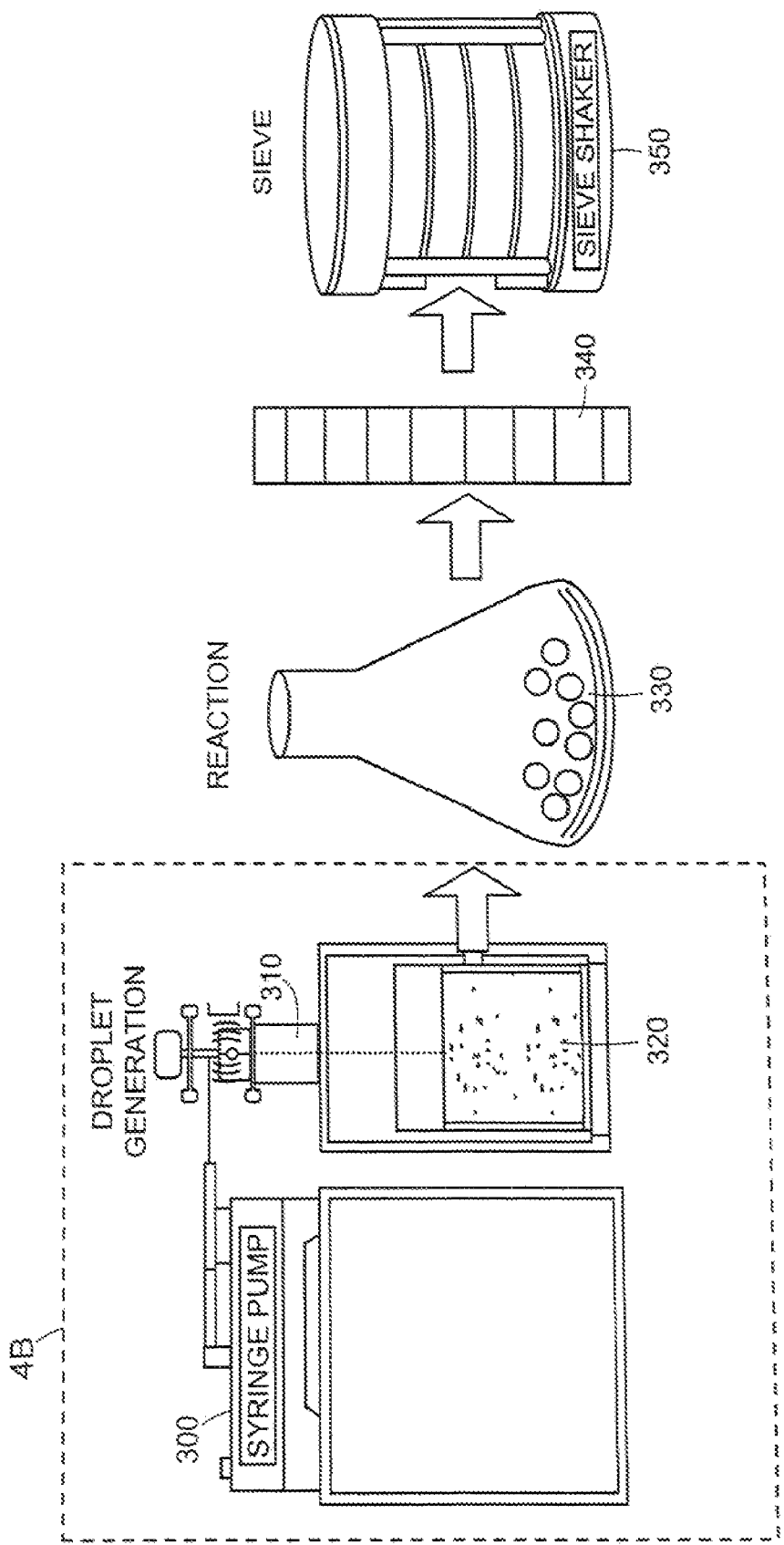
FIG. 4A is a schematic of the manufacture of a composition.

Referring to FIG. 4A, a system for manufacturing particles includes a flow controller 300, a drop generator 310, a gelling vessel 320, a reactor vessel 330, a gel dissolution chamber 340 and a filter 350. The flow controller 300 delivers polymer solutions to a viscosity controller 305, which heats the solution to reduce viscosity prior to delivery to the drop generator 310. The drop generator 310 forms and directs drops into a gelling vessel 320, where drops are stabilized by gel formation. The gel-stabilized drops are transferred from the gelling vessel 320 to reactor vessel 330 where the polymer in the gel-stabilized drops is reacted forming precursor particles. The precursor particles are transferred to a gel dissolution chamber 340, where the gel is dissolved. The particles are then filtered in a filter 350 to remove debris, sterilized, and packaged.

A base polymer and a gelling precursor are dissolved in water and mixed. The mixture is introduced to a high pressure pumping apparatus, such as a syringe pump (e.g., model PHD4400, Harvard Apparatus, Holliston, Mass.). Examples of base polymers include polyvinyl alcohol, polyacrylic acid, polymethacrylic acid, poly vinyl sulfonate, carboxymethyl cellulose, hydroxyethyl cellulose, substituted cellulose, polyacrylamide, polyethylene glycol, polyamides, polyureas, polyurethanes, polyester, polyeters, polystyrene, polysaccharide, polylactic acid, polyethylene, polymethylmethacrylate and copolymers or mixtures thereof. A preferred polymer is polyvinyl alcohol. The polyvinyl alcohol, in particular, is hydrolyzed in the range of 80 to 99%. The weight average molecular weight of the base polymer can be in the range of 9000 to 186,000, 85,000 to 146,000 or 89,000 to 98,000. Gelling precursors include, for example, alginates, alginate salts, xanthan gums, natural gum, agar, agarose, chitosan, carrageenan, fucoidan, furcellaran, laminaran, hypnea, eucheuma, gum arabic, gum ghatti, gum karaya, gum tragacanth, hyaluronic acid, locust beam gum, arabinogalactan, pectin, amylopectin, other water soluble polysaccharides and other ionically crosslinkable polymers. A particular gelling precursor is sodium alginate. A preferred sodium alginate is high guluronic acid, stem-derived alginate (e.g. about 50 or 60% or more guluronic acid with a low viscosity e.g. about 20 to 80 cps at 20° C.) which produces a high tensile, robust gel. High molecular weight PVA is dissolved in water by heating, typically above about 70° C., while alginates can be dissolved at room temperature. The PVA can be dissolved by mixing PVA and alginate together in a vessel which is heated to autoclave temperature (about 121° C.). Alternatively, the PVA can be disposed in water and heated and the alginate subsequently added at room temperature to avoid exposing the alginate to high temperature. Heat can also be applied by microwave application. In embodiments, for PVA/alginate, the mixture is typically about 7.5 to 8.5%, e.g. about 8% by weight PVA and about 1.5 to 2.5%, e.g. about 2%, by weight alginate.

Figure 4B:
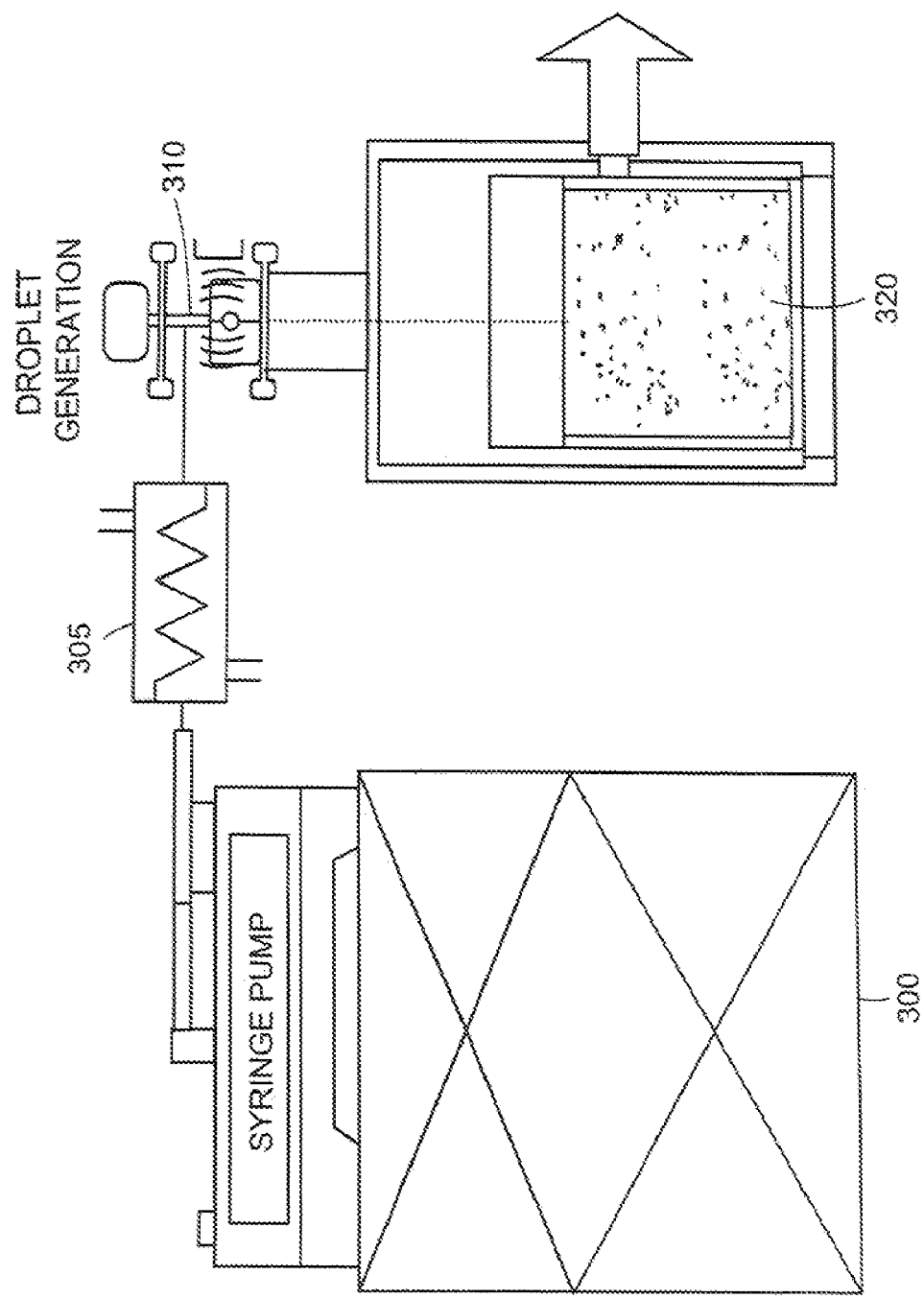
FIG. 4B is an enlarged schematic of region A in FIG. 4A.

Referring to FIG. 4B, the viscosity controller 305 is a heat exchanger circulating water at a predetermined temperature about the flow tubing between the pump and drop generator. The mixture of base polymer and gelling precursor flows into the viscosity controller 305, where the mixture is heated so that its viscosity is lowered to a level for efficient formation of very small drops. For a high molecular weight PVA/alginate solution, the temperature of the circulating water is less than about 75° C. and more than about 60° C., for example, 65° C. which maintains the mixture at a viscosity of 90-200 centipoise. For spherical particles, the viscosity of the drops is maintained so they are captured in the gelling vessel without splintering or cojoining which can create irregular, fiberous particles. In other embodiments, the flow controller and/or the drop generator can be placed in a temperature-controlled chamber, e.g. an oven, or a heat tape wrap, to maintain a desired viscosity.

The drop generator 310 generates substantially spherical drops of predetermined diameter by forcing a stream of the mixture of base polymer and gelling precursor through a nozzle which is subject to a periodic disturbance to break up the jet stream into drops. The jet stream can be broken into drops by vibratory action generated for example, by an electrostatic or piezoelectric element. The drop size is controlled by controlling the flow rate, viscosity, amplitude, and frequency at which the element is driven. Lower flow rates and higher frequencies produce smaller drops. A suitable electrostatic drop generator is available from NISCO Engineering, model NISCO Encapsulation unit VAR D, Zurich, Switzerland. In embodiments, the frequency is in the range of about 0.1 to 0.8 kHz. The flow rate through the droplet generator is in the range of about 1 to 12 mL per minute. The drop generator can include charging the drops after formation such that mutual repulsion between drops prevents drop aggregation as drops travel from the generator to the gelling vessels. Charging may be achieved by, e.g. an electrostatic charging device such as a charged ring positioned downstream of the nozzle.

Drops of the base polymer and gelling precursor mixture are captured in the gelling vessel 320. The gelling vessel 320 contains a gelling agent which interacts with the gelling precursor to stabilize drops by forming a stable gel. Suitable gelling agents include, for example, a divalent cation such as alkali metal salt, alkaline earth metal salt or a transition metal salt that can ionically crosslink with the gelling agent. An inorganic salt, for example, a calcium, barium, zinc or magnesium salt can be used as a gelling agent. In embodiments, particularly those using an alginate gelling precursor, a suitable gelling agent is calcium chloride. The calcium cations have an affinity for carboxylic groups in the gelling precursor. The cations complex with carboxylic groups in the gelling precursor resulting in encapsulation of the base polymer in a matrix of gelling precursor.

Figure 5:
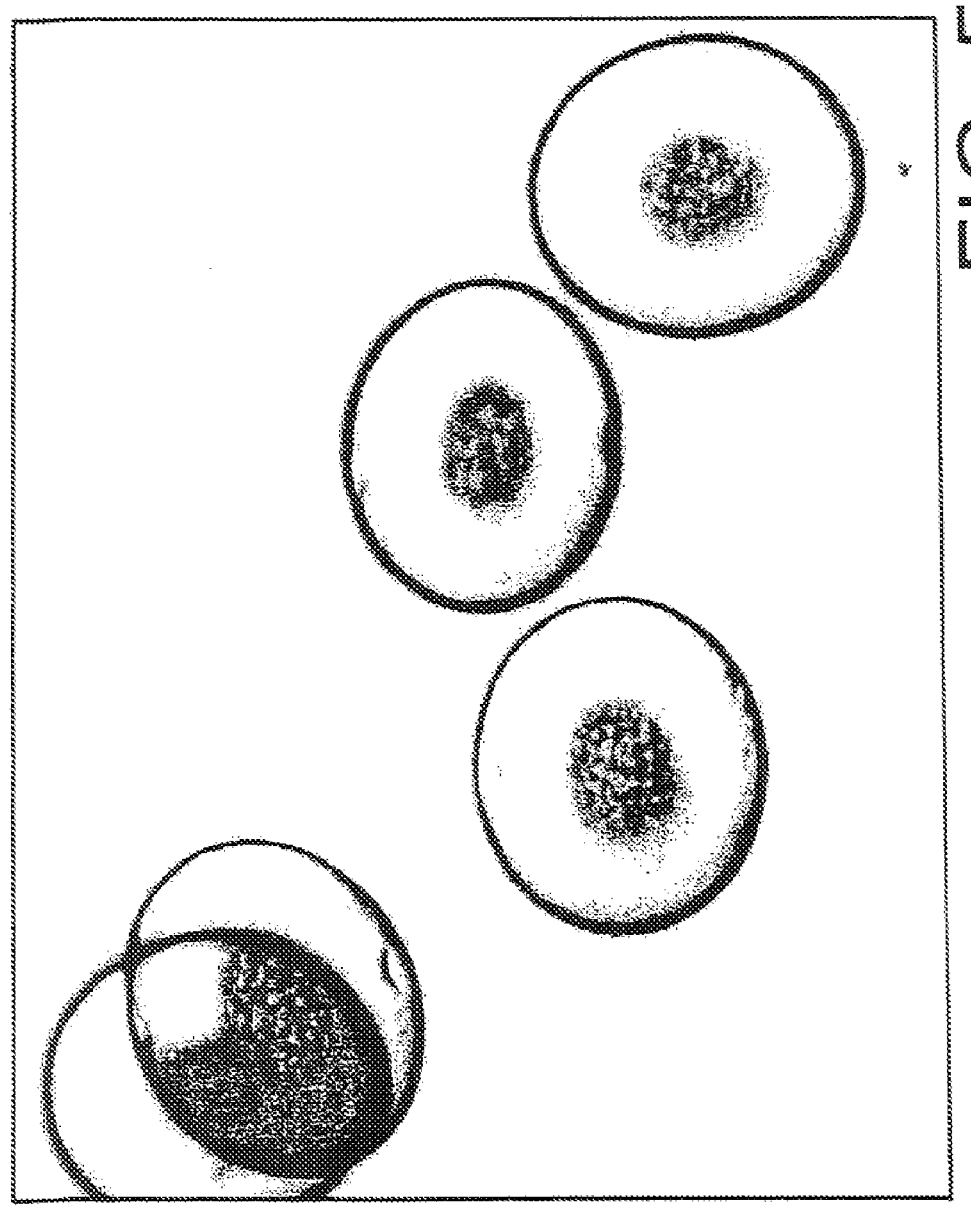
FIG. 5 is a photograph of gel-stabilized drops.

Referring to FIG. 5, a photo-image of the gelled particles, the gelling agent is in an amount selected in accordance with the desired properties of the particles. As evident, a pore structure in the particle forms in the gelling stage. The concentration of the gelling agent can control pore formation in the particle, thereby controlling the porosity gradient in the particle. Adding non-gelling ions, for example, sodium ions, to the gelling solution can reduce the porosity gradient, resulting in a more uniform intermediate porosity throughout the particle. In embodiments, the gelling agent is, for example, 0.01-10 weight percent, 1-5 weight percent or 2 weight percent in deionized water. In embodiments, particles, including gelling agent and a pore structure can be used in composition 27.

Following drop stabilization, the gelling solution is decanted from the solid drops and the stabilized drops are transferred to the reactor vessel 330. In the reactor vessel 330, the stabilized drops are reacted to produce precursor particles. The reactor vessel includes an agent that chemically reacts with the base polymer, e.g. to cause crosslinking between polymer chains and/or within a polymer chain. The agent diffuses into the stabilized drops from the surface of the particle in a gradient which, it is believed, provides more crosslinking near the surface of the stabilized drop compared to the body and center of the drop. Reaction is greatest at the surface of the drop, providing a stiff, abrasion resistant exterior. For polyvinyl alcohol, for example, the vessel 330 includes aldehydes, such as formaldehyde, glyoxal, benzaldehyde, aterephthalaldehyde, succinaldehyde and glutaraldehyde for the acetalization of polyvinyl alcohol. The vessel 330 also includes an acid, for example, strong acids such as sulfuric acid, hydrochloric acid, nitric acid and weak acids such as acetic acid, formic acid and phosphoric acid. In embodiments, the reaction is primarily a 1,3 acetalization:

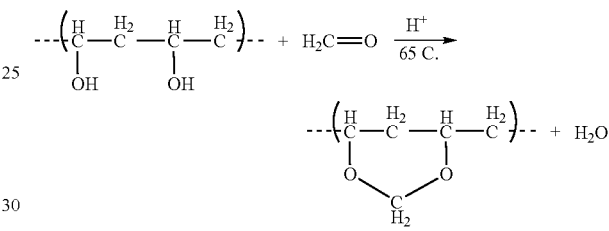

This intra-chain acetalization reaction can be carried out with relatively low probability of inter-chain crosslinking as described in John G. Pritchard "Poly(Vinyl Alcohol) Basic Properties And Uses (Polymer Monograph, vol. 4) (see p. 93-97), Gordon and Breach, Science Publishers LTD., London, 1970, the entire contents of which is hereby incorporated by reference. Some OH groups along a polymer chain can remain unconverted since the reaction proceeds in a random fashion and there can be left over OH groups that do not react with adjacent groups.

Adjusting the amount of aldehyde and acid used, reaction time and reaction temperature can control the degree of acetalization. In embodiments, the reaction time is e.g., 5 minutes to 1 hour, 10 to 40 minutes or 20 minutes. The reaction temperature can be 25° C. to 150° C. or 75° C. to 130° C. or 65° C. The reactor vessel is placed in a water bath fitted with an orbital motion mixer. The crosslinked precursor particles are washed several times with deionized water to neutralize the particles and remove any residual acidic solution.

The precursor particles are transferred to the dissolution chamber 340 to remove the gelling precursor, e.g. by an ion exchange reaction. In embodiments, sodium alginate is removed by ion exchange with a solution of sodium hexa-metaphosphate (EM Science). The solution can include, for example, ethylenediaminetetraacetic acid (EDTA), citric acid, other acids and phosphates. The concentration of the sodium hexa-metaphosphate can be, for example, 1-20 weight %, 1-10 weight % or 5 weight % in deionized water. Residual gelling precursor, for example, sodium alginate, can be determined by assay for detection of uronic acids in, for example, alginates containing mannuronic and guluronic acid residues. Suitable assays include rinsing the particles with sodium tetraborate in sulfuric acid solution to extract alginate and combining the extract with metahydroxydiphenyl colormetric reagent and determining concentration by UV/VIS spectroscopy. Testing can be carried out by alginate suppliers such as FMC Biopolymer, Oslo, Norway. Residual alginate can be present in the range of about 20-35% by weight prior to rinsing and in the range of about 0.01-0.5% or 0.1-0.3% or 0.18% in the particles after rinsing for 30 minutes in water at about 23° C.

The particles are filtered through filter 350 to remove residual debris. Particles of 500 to 700 microns are filtered through a sieve of 710 microns and then a sieve of 300 microns. Particles of 700 to 900 microns are filtered through a sieve of 1000 microns and then a sieve of 500 microns. Particles of 900 to 1200 microns are filtered through a sieve of 1180 microns and then a sieve of 710 microns.

The filtered particles are sterilized by a low temperature technique such as e-beam irradiation, and packaged. In embodiments, electron beam irradiation can be used to pharmaceutically sterilize the particles to reduce bioburden. In e-beam sterilization, an electron beam is accelerated using magnetic and electric fields, and focused into a beam of energy. This resultant beam can be scanned by means of an electromagnet to produce a "curtain" of accelerated electrons. The accelerated electron beam penetrates the collection of particles to confer upon them electrons which destroy bacteria and mold to sterilize and reduce the bioburden in the particles. Electron beam sterilization can be performed by sterilization vendors, such as Titan Scan, Lima, Ohio.

Additional information about the particles is described in commonly assigned U.S. Ser. No. 10/215,594, filed Aug. 9, 2002, and entitled "Embolization", hereby incorporated by reference in its entirety.

The following example is illustrative and not intended to be limiting.

EXAMPLE

Particles are manufactured from an aqueous solution containing 8 weight % of polyvinyl alcohol, 99+% hydrolyzed, average $M_w$ 89,000-120,000 (ALDRICH) and 2 weight % of gelling precursor, sodium alginate, PRONOVA UPLVG, (FMC BioPolymer, Princeton, N.J.) in deionized water and the mixture is heated to about 121° C. The solution has a viscosity of about 310 centipoise at room temperature and a viscosity of about 160 cps at 65° C. Using a syringe pump (Harvard Apparatus), the mixture is fed to drop generator (Nisco Engineering). Drops are directed into a gelling vessel containing 2 weight % of calcium chloride in deionized water and stirred with a stirring bar. The calcium chloride solution is decanted within about three minutes to avoid substantial leaching of the polyvinyl alcohol from the drops into the solution. The drops are added to the reaction vessel containing a solution of 4% by weight of formaldehyde (37 wt % in methanol) and 20% by weight sulfuric acid (95-98% concentrated). The reaction solution is stirred at 65° C. for 20 minutes. Precursor particles are rinsed with deionized water (3×300 mL) to remove residual acidic solution. The sodium alginate is substantially removed by soaking the precursor particles in a solution of 5 weight % of sodium hexa-methaphosphate in deionized water for 0.5 hour. The solution is rinsed in deionized water to remove residual phosphate and alginate. The particles are filtered by sieving, as discussed above, placed in saline (USP 0.9% NaCl) and followed by irradiation sterilization.

Particles were produced at the nozzle diameters, nozzle frequencies and flow rates (amplitude about 80% of maximum) described in Table 1.

TABLE 1

| Bead Size (microns) | Nozzle Diameter (microns) | Frequency (kHz) | Flow Rate (mL/min) | Density (g/mL) | Sphericity | Suspendability (minutes) |
|---|---|---|---|---|---|---|
| 500-700 | 150 | 0.45 | 4 | — | 0.92 | 3 |
| 700-900 | 200 | 0.21 | 5 | 1.265 | 0.94 | 5 |
| 900-1200 | 300 | 0.22 | 10 | — | 0.95 | 6 |

Suspendability is measured at room temperature by mixing a solution of 2 ml of particles in 5 ml saline with contrast solution (Omnipaque 300, Nycomed, Buckinghamshire, UK) and observing the time for about 50% of the particles to enter suspension, i.e. have not sunk to the bottom or floated to the top of a container (about 10 ml, 25 mm diameter vial). Suspendability provides a practical measure of how long the particles will remain suspended. (Omnipaque is an aqueous solution of Iohexol, N.N.-Bis (2,3-dihydroxypropyl)-T-[N-(2,3-dihydroxypropyl)-acetamide]-2,4,6-trilodo-isophthalamide; Omnipaque 300 contains 647 mg of iohexol equivalent to 300 mg of organic iodine per ml. The specific gravity of 1.349 of 37° C. and an absolute viscosity 11.8 cp at 20° C.) The particles remain in suspension for about 2 to 3 minutes.

Particle size uniformity and sphericity is measured using a Beckman Coulter RapidVUE Image Analyzer version 2.06 (Beckman Coulter, Miami, Fla.). Briefly, the RapidVUE takes an image of continuous-tone (gray-scale) form and converts it to a digital form through the process of sampling and quantization. The system software identifies and measures particles in an image in the form of a fiber, rod or sphere. Sphericity computation and other statistical definitions are in Appendix A, attached, which is a page from the RapidVUE operating manual.

Figure 6:
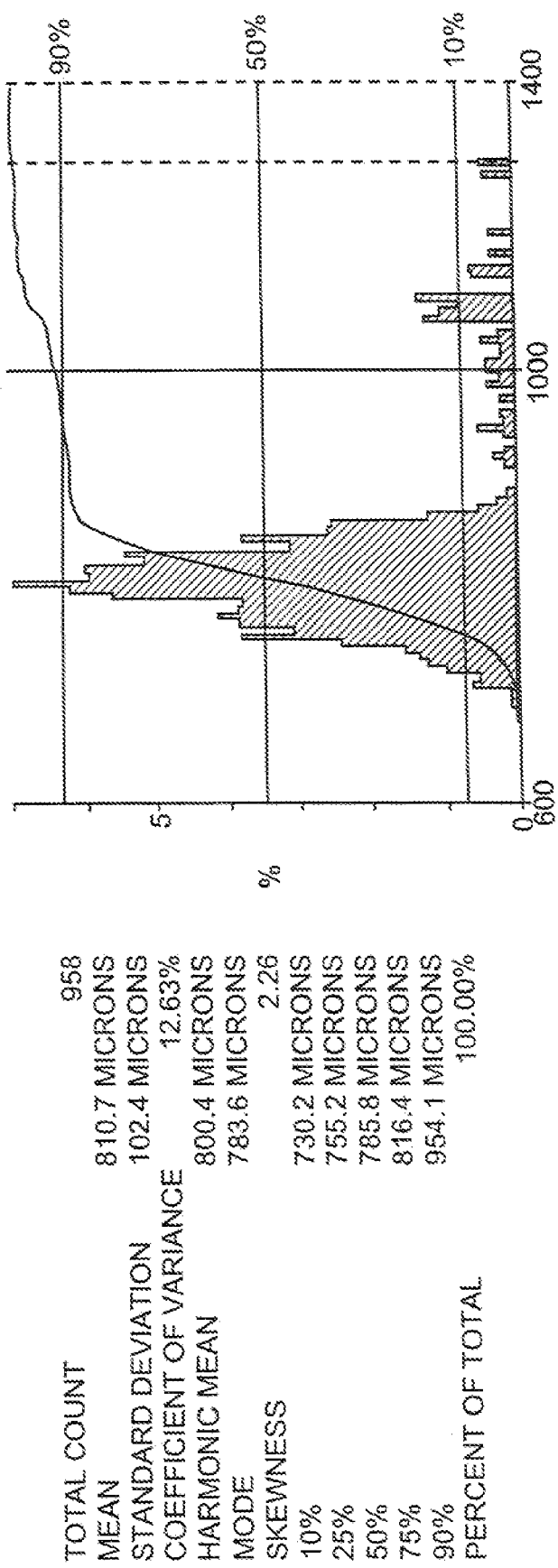
FIG. 6 is a graph of particle size uniformity.

Referring to FIG. 6, particle size uniformity is illustrated for particles 700-900 micron. The x-axis is the particle diameter. The y-axis is the volume normalized percentage of particles at each particle size. The total volume of particles detected is computed and the volume of the particles at each diameter is divided by the total volume. The particles have distribution of particle sizes with variance of less than about ±15%.

While substantially spherical particles are preferred, non-spherical particles can be manufactured and formed by controlling, e.g., drop formation conditions or by post-processing the particles, e.g. by cutting or dicing into other shapes. Particles can also be shaped by physical deformation followed by crosslinking. Particle shaping is described in U.S. Ser. No. 10/116,330, filed Apr. 4, 2002.

Carrier: Composition 27 can include one or more carrier materials that allow the composition to be delivered in a first state, e.g., a relatively fluid or low viscosity state, and change, e.g., by phase transition, to a second state, e.g., a relatively high viscosity or rigid state. In embodiments, particles 25 can be suspended in a biocompatible, resorbable lubricant, such as a cellulose polysaccharide gel having water, glycerin and sodium carboxymethylcellulose. The gel enables particles 25 to remain in suspension without settling. Other polysaccharides can also be included such as cellulose, agar methylcellulose, hydroxypropyl methylcellulose, ethylcellulose, microcrystalline cellulose, oxidized cellulose, and other equivalent materials.

The polysaccharide gel is biocompatible, and the lubricious nature of the polysaccharide gel can reduce the frictional forces generated during the transferring of the particles from a syringe by injection into the tissue site. In addition, polysaccharides do not generate an antigenic response, and the polysaccharide gel is readily sterilizable and stable at ambient conditions and does not need refrigeration for storage and shipment.

After injection of composition 27 into the tissue, the polysaccharide gel can be resorbed by the tissue, leaving the non-resorbable matrix of particles 25 in place in the particular area or bolus, where it can remain without migrating to other areas of the body.

Other examples of carriers include undiluted agarose, methyl cellulose or other linear unbranched polysaccharide, dextran sulfate, succinylated non-crosslinked collagen, methylated non-crosslinked collagen, glycogen, dextrose, maltose, triglycerides of fatty acids, egg yolk phospholipids, heparin, DMSO, phosphate buffered saline, and the like. Examples of collagen are described in U.S. Pat. No. 5,490,984. More examples of appropriate carriers include hyaluronic acid, polyvinyl pyrrolidone or a hydrogel derived thereof, dextran or a hydrogel derivative thereof, glycerol, polyethylene glycol, succinylated collagen, liquid collagen, oil based emulsions such as corn oil or safflower, B-D glucose (or B-glucan, as described in U.S. Pat. No. 6,277,392) or other polysaccharides or biocompatible organic polymers either singly or in combination with one or more of the above materials.

Hydrogel compositions, such as those that swell upon injection into tissue due to hydration by physiologic fluid, are described, for example, in U.S. Pat. No. 6,423,332; U.S. Pat. Nos. 6,306,418; and 5,902,932. In embodiments, the composition can swell from an initial dehydrated volume to a final hydrated volume that is substantially the same as the initial total volume of composition injected into the tissue to be treated. Examples include poly(ethylene oxide), polyvinyl pyrrolidone, polyvinyl alcohol, poly(propylene oxide), poly(ethylene, glycol), polypropylene glycol), polytetramethylene oxide, polyacrylamide, poly(hydroxy ethyl acrylate), poly(hydroxy ethyl methacrylate), hydroxy ethyl cellulose, hydroxy propyl cellulose, methoxylated pectin gels, agar, a starch such as cornstarch, a modified starch, an alginate, a hydroxy ethyl carbohydrate, or the like and should preferably be adjusted so as to allow swelling to a selected percent after hydration. The carrier can disperse over time.

In some embodiments, composition 27 includes between about 0.5 to about 50 weight percent of the carrier. For example, composition 27 can include greater than or equal to about 0.5, 5, 10, 15, 20, 25, 30, 35, 40, or 45 weight percent of the carrier; and/or less than or equal to about 50, 45, 40, 35, 30, 25, 20, 15, 10, or 5 weight percent of the carrier.

Contrasting agent: In embodiments, composition 27 includes a contrasting agent. The contrast agent can be a biocompatible material capable of being monitored during injection by, for example, radiography, fluoroscopy, ultrasound, or visually. The contrast agent can be water soluble or water insoluble. Examples of water soluble contrast agents include metrizamide, iopamidol, iothalamate sodium, iodomide sodium, and meglumine. Examples of water insoluble contrast agents include tantalum, tantalum oxide, and barium sulfate, each of which is available in a form for in vivo use including a particle size of about 10 microns or less. Other water insoluble contrast agents include gold, tungsten, and platinum powders.

Some examples of radiopaque materials include paramagnetic materials (e.g. persistent free radicals) and compounds, salts, and complexes of paramagnetic metal species (e.g., transition metal or lanthanide ions); heavy atom (e.g., atomic number of 37 or more) compounds, salts, or complexes (e.g., heavy metal compounds, iodinated compounds, etc.); radionuclide containing compounds, salts, or complexes (e.g. salts, compounds or complexes of radioactive metal isotopes or radiodinated organic compounds); and superparamagentic materials (e.g., metal oxide or mixed oxide particles, particularly iron oxides). Paramagnetic metals include Gd (III), Dy (III), Fe (II), Fe (III), Mn (III) and Ho (III), and paramagnetic Ni, Co and Eu species. Heavy metals include Pb, Ba, Ag, Au, W, Cu, Bi and lanthanides such as Gd. Metals, metal oxides, and alloys, including but not limited to medical grade stainless steel, silver, gold, titanium and titanium alloys, oxide derivatives of stainless steel or titanium or titanium alloys, aluminum oxide, and zirconium oxide can also be used. The amount of contrasting agent used can be any amount sufficient to be detected.

Therapeutic agent: In embodiments, particles 25 include one or more therapeutic agents. For example, an effective amount of wound healing agents can be added to composition 27. These agents include protein growth factors such as fibroblast growth factors (FGFs), platelet derived growth factors (PDGFs), epidermal growth factors (EGFs), connective tissue activated peptides (CTAPs), transforming growth factors (TGFs), and the like. The amount of wound healing agent(s) to be included with composition 27 can vary, depending, for example, on the patient (age, sex, medical history) and the site being treated. In embodiments, composition 27 includes antimicrobial additives and/or antibodies to reduce the potential for infection at the treatment site. Other agents are described in commonly assigned U.S. Ser. No. 10/232,265, filed on Aug. 30, 2002, and entitled "Drug Delivery Particles". The therapeutic agent can be added to composition 27 and/or be placed on particles 25.

Other additives: Composition 27 can include one or more materials that enhance the mechanical and/or physical properties of the composition. In some embodiments, particles 25 can be combined with one or more relatively hard materials. The relatively hard material can be, for example, biocompatible ceramics, biocompatible metals (e.g., stainless steel), glass, or other biocompatible materials such as calcium salts, e.g., hydroxyapatite. The combination of particles 25 and hard material(s) can be used, for example, to fill depressed scars, unsymmetrical orbital floors, or bone defects in reconstructive surgical procedures.

Other methods can be used to placed particles 25 and/or composition 27 into tissue. For example, particles 25 and/or composition 27 can be placed laproscopically. Particles 25 and/or composition 27 can also be placed in a cavity or void created in tissue.

Referring to FIGS. 7A-7F, a method of placing particles 25 and/or composition 27 is shown. The method includes using a catheter or a sheath 402, e.g., a blunt-ended hypotube, configured to proximally receive a penetration device 404, e.g., one having a trocar at its distal end. Penetration device 404 is inserted into sheath 402 to allow the sheath to penetrate into tissue 403 (FIG. 7A). In embodiments, the penetration depth can be determined by striping 406 formed on sheath 402. For example, the tip of penetration device 404 can penetrate about 2-2.5 cm into tissue 403, while the tip of sheath 402 can penetrate about 0.5-1 cm into the tissue. After penetration of tissue 403, penetration device 404 is withdrawn from sheath 402, which is retained penetrated in the tissue (FIG. 7B).

A catheter 406 carrying an uninflated balloon 408 at the distal end is then inserted into sheath 402 (FIG. 7C) such that the balloon extends into tissue 403. Balloon 408 is then inflated using an inflation device, such as a syringe 410 containing saline (FIG. 7D). As balloon 408 inflates, it creates a cavity or a void 412 in tissue 403. In embodiments, balloon 408 is shaped to provide a cavity with a predetermined shape. Balloon 408 is then deflated, and catheter 406 is withdrawn from sheath 402 (FIG. 7E). An injection device 414, such as a syringe 416 containing particles 25 and/or composition 27, is then inserted into sheath 402, and the particles and/or composition can be delivered to cavity 412 (FIG. 7F).

In other embodiments, particles 25 and/or composition 27 can be used with a device, such as an indwelling sling, used to treat urinary incontinence. An example of a device is described in WO 00/74633. Particles 25 and/or composition 27 can be placed, e.g., injected, into the device as a bulking agent to provide lift, thereby providing another method of adjusting the degree of support provided by the device.

All publications, references, applications, and patents referred to herein are incorporated by reference in their entirety.

Other embodiments are within the claims.

What is claimed is:

1. A method of treating tissue, the method comprising:
    placing substantially spherical polymer particles in the tissue, the particles having an interior region comprising pores having a predominant pore size in the range of about 20 to 35 microns, a first region substantially surrounding the interior region comprising pores having a predominant pore size in the range of about 2 to 18 microns, and a third region surrounding the second region comprising pores having a predominant pore size of about 2 microns or less,
    wherein the polymer comprises crosslinked polyvinyl alcohol.
2. The method of claim 1, wherein the particles are injected into the tissue.
3. The method of claim 2, wherein the particles are injected percutaneously.
4. The method of claim 1, wherein the particles are delivered through a catheter.
5. The method of claim 1, comprising forming a cavity in the tissue, and placing the particles in the cavity.
6. The method of claim 1, wherein the tissue is adjacent to a body passageway.
7. The method of claim 6, wherein the passageway is defined by a ureter.
8. The method of claim 1, wherein the tissue is adjacent to a body passageway, the particles being placed in an amount effective to narrow the passageway.
9. The method of claim 1, wherein the polyvinyl alcohol is 1,3 diol acetalized.
10. The method of claim 1, wherein the particles comprise a polysaccharide.
11. The method of claim 1, wherein the polysaccharide comprises alginate.
12. The method of claim 1, wherein the particles comprise a therapeutic agent.
13. A method of treating an individual, the method comprising:
    placing a therapeutically effective amount of substantially spherical particles comprising polyvinyl alcohol in a tissue of the individual, the particles having an interior region comprising pores having a predominant pore size in the range of about 20 to 35 microns, a first region substantially surrounding the interior region comprising pores having a predominant pore size in the range of about 2 to 18 microns, and a third region surrounding the second region comprising pores having a predominant pore size of about 2 microns or less,
    wherein the polymer comprises crosslinked polyvinyl alcohol.
14. The method of claim 13, further comprising selecting the individual diagnosed with gastroesophageal reflux disease.
15. The method of claim 14, wherein the tissue is adjacent to a gastrointestinal tract.
16. The method of claim 13, further comprising selecting the individual diagnosed with vesicoureteral reflux.
17. The method of claim 16, wherein the tissue is adjacent to a ureter.
18. The method of claim 13, further comprising selecting the individual diagnosed with urinary incontinence.
19. The method of claim 13, further comprising selecting the individual diagnosed with fecal incontinence.
20. The method of claim 13, wherein the particles are placed percutaneously.
21. The method of claim 13, wherein the particles are placed through a catheter.
22. The method of claim 13, further comprising selecting the individual diagnosed with instrinsic sphincteric deficiency.
23. The method of claim 13, further comprising selecting the individual diagnosed with vocal cord paralysis.
24. The method of claim 13, further comprising selecting the individual in need of a reconstructive or cosmetic procedure.
25. The method of claim 1, wherein, for at least some of the plurality of particles, each particle has a different radius.
26. The method of claim 13, wherein, for at least some of the therapeutically effective amount of particles, each particle has a different radius.

* * * * *

UNITED STATES PATENT AND TRADEMARK OFFICE
CERTIFICATE OF CORRECTION

PATENT NO.         : 7,611,542 B2
APPLICATION NO.    : 11/555413
DATED              : November 3, 2009
INVENTOR(S)        : George Bourne et al.

It is certified that error appears in the above-identified patent and that said Letters Patent is hereby corrected as shown below:

Title Page, (56) References Cited, U.S. Patent Documents, Entry 3, Column 3:
Delete "Nishimura etal." and insert --Nishimura et al.--.

Column 16, Claim 22, Line 39: Delete "instrinsic" and insert --intrinsic--.

Signed and Sealed this

Twenty-second Day of December, 2009

David J. Kappos
*Director of the United States Patent and Trademark Office*